(12) United States Patent
Jalkanen et al.

(10) Patent No.: US 7,354,577 B2
(45) Date of Patent: Apr. 8, 2008

(54) COMMON LYMPHATIC ENDOTHELIAL AND VASCULAR ENDOTHELIAL RECEPTOR-1 (CLEVER-1) AND USES THEREOF

(75) Inventors: Sirpa Jalkanen, Piispanristi (FI); Heikki Irjala, Turku (FI); Marko Salmi, Turku (FI)

(73) Assignee: Faron Pharmaceuticals Oy, Turku (FI)

( * ) Notice: Subject to any disclaimer, the term of this patent is extended or adjusted under 35 U.S.C. 154(b) by 73 days.

(21) Appl. No.: 10/497,991

(22) PCT Filed: Jan. 8, 2003

(86) PCT No.: PCT/FI03/00010

§ 371 (c)(1),
(2), (4) Date: Nov. 30, 2004

(87) PCT Pub. No.: WO03/057130

PCT Pub. Date: Jul. 17, 2003

(65) Prior Publication Data

US 2005/0069888 A1 Mar. 31, 2005

(51) Int. Cl.
*A61K 39/395* (2006.01)
(52) U.S. Cl. .............................. 424/130.1; 424/143.1; 424/153.1
(58) Field of Classification Search ............... None
See application file for complete search history.

(56) References Cited

U.S. PATENT DOCUMENTS

| | | | |
|---|---|---|---|
| 5,484,596 A * | 1/1996 | Hanna et al. | 424/277.1 |
| 5,840,844 A | 11/1998 | Lasky et al. | |
| 6,166,179 A | 12/2000 | Rice et al. | |
| 6,713,059 B2 * | 3/2004 | Kende et al. | 424/150.1 |
| 2003/0108984 A1 * | 6/2003 | Naor et al. | 435/69.1 |

FOREIGN PATENT DOCUMENTS

WO WO 00/39166 A1 7/2000

OTHER PUBLICATIONS

Salmi et al CLEVER-1 mediates lymphocyte transmigration through vascular and lymphatic endothelium. Blood. Dec. 15, 2004;104(13):3849-57.*
Norman and Kubes Therapeutic intervention in inflammatory diseases: a time and place for anti-adhesion therapy. Microcirculation. Jan-Feb. 2005;12(1):91-8.*
Kzhyshkowska et al. Stabilin-1, a homeostatic scavenger receptor with multiple functions. J Cell Mol Med. Jul.-Sep. 2006;10(3):635-49.*
Prevo et al. Rapid plasma membrane-endosomal trafficking of the lymph node sinus and high endothelial venule scavenger receptor/homing receptor stabilin-1 (FEEL-1/CLEVER-1). J Biol Chem. Dec. 10, 2004;279(50):52580-92.*

Lerner RA, Tapping the immunological repertoire to produce antibodies of predetermined specificity. Nature 1982; 299:593-596, see p. 595-596.*
Adachi, H. and Tsujimoto, M., "FEEL-1, a Novel Scavenger Receptor with in Vitro Bacteria-binding and Angiogenesis-modulating Activities," *J. Biol. Chem.* 277:34264-34270, The American Society for Biochemistry and Molecular Biology, Inc. (Sep. 2002).
Database EM-HUM Online, Accession No. HSD433, retrieved from EBI (created 1996, as updated Jul. 5, 2002).
Sequence comparison between Database EM-HUM Online, Accession No. HSD433, retrieved from EBI (Document No. AT1) (created 1996, as updated Jul. 5, 2002) with SEQ ID No. 1.
Database SWALL Online, Accession No. Q93072, retrieved from EBI (created 1997, as updated Jun. 1, 2003).
Sequence comparison between Database SWALL Online, Accession No. Q93072, retrieved from EBI (Document No. AS2) (created 1997, as updated Jun. 1, 2003) with the protein sequence of SEQ ID No. 1.
Nagase, T., et al., "Prediction of the Coding Sequences of Unidentified Human Genes. VI. The Coding Sequences of 80 New Genes (KIAA0201-KIAA0280) Deduced by Analysis of cDNA Clones from Cell Line KG-1 and Brain," *DNA Res.* 3:321-329, Kazusa DNA Research Institute and Universal Academy Press (1996).
Database EM-HUM Online, Accession No. HSA275213, retrieved from EBI (created 1999, as updated Feb. 14, 2003).
Sequence comparison between Database EM-HUM Online, Accession No. HSA275213, retrieved from EBI (Document No. AS3) (created 1999, as updated Feb. 14, 2003) with SEQ. ID. No. 1.
Database SWALL Online, Accession No. Q9NY15, retrieved from EBI (created 2000, as updated Jun. 1, 2003).
Sequence comparison between Database SWALL Online, Accession No. Q9NY15, retrieved from EBI (Document No. AR4) (created 2000, as updated Jun. 1, 2003) with the protein sequence of SEQ. ID. No. 1.
Database GSN Online, Accession No. AAA57362, retrieved from EBI (2000).
Sequence comparison between Database GSN Online, Accession No. AAA57362, retrieved from EBI (Document No. AT4) (2000) with SEQ. ID. No. 1 lacking nucleotides 2914-3009.
Sequence comparison between Database GSN Online, Accession No. AAA57362, retrieved from EBI (Document No. AT4) (2000) with SEQ. ID. No. 1.
Database GSP Online, Accession No. AAY93910, retrieved from EBI (2000).

(Continued)

*Primary Examiner*—Maher M. Haddad
(74) *Attorney, Agent, or Firm*—Sterne, Kessler, Goldstein & Fox P.L.L.C.

(57) ABSTRACT

A novel protein Common Lymphatic Endothelial and Vascular Endothelial Receptor-1 (CLEVER-1) is described. CLEVER-1 mediates leukocyte and malignant cell binding to vascular and lymphoid endothelial cells. CLEVER-1 is the first protein that has been reported to mediate both influx into and efflux from the lymph nodes. Also provided are methods of treating inflammation and preventing metastasis of malignant cells by providing an inhibitor of CLEVER-1 binding.

7 Claims, 12 Drawing Sheets

OTHER PUBLICATIONS

Sequence comparison between Database GSP Online, Accession No. AAY93910, retrieved from EBI (Document No. AT5) (2000) with SEQ. ID. No. 1 lacking nucleotides 2914-3009.

Sequence comparison between Database GSP Online, Accession No. AAY93910, retrieved from EBI (Document No. AT5) (2000) with SEQ. ID. No. 1.

Johanasson, I.H., et al, "Mechanisms of lymphocyte exit from lymphoid tissues," *Immunol. Lett., Abstracts of the 14th European Immunology Meeting EFIS 2000*, Abstract No. 391, pp. 170, Elsevier/North Holland Biomedical Press (2000).

Database SWALL Online, Accession No. Q93073, retrieved from EBI (created 1997, as updated Jul. 5, 2004).

* cited by examiner

| Antibody: | 3-266 | 3-372 | | 3G6 |

200 kDa —

Fig. 2

A  Tumor cell binding to HEVs:

B  Tumor cell binding to lymphatic endothelium:

```
actctgtcct ggacagcgtg cccaccagcc atg gcg ggg ccc cgg ggc ctc ctc      54
cca ctc tgc ctc ctg gcc ttc tgc ctg gca ggc ttc agc ttc gtc agg      102
ggg cag gtg ctg ttc aaa ggc tgt gat gtg aaa acc acg ttt gtc act      150
cat gta ccc tgc acc tcg tgc gcg gcc atc aag aag cag acg tgt ccc      198
tca ggc tgg ctg cgg gag ctc ccg gat cag ata acc cag gac tgc cgc      246
tac gaa gta cag ctg ggg ggc tct atg gtg tcc atg agc ggc tgc aga      294
cgg aag tgc cgg aag caa gtg gtg cag aag gcc tgc tgc cct ggc tac      342
tgg ggt tcc cgg tgc cat gaa tgc cct ggg ggc gct gag acc cca tgc      390
aat ggc cac ggg acc tgc ttg gat ggc atg gac agg aat ggg acc tgt      438
gtg tgc cag gaa aac ttc cgc ggc tca gcc tgc cag gag tgc caa gac      486
ccc aac cgg ttc ggg cct gac tgc aa tcg gtg tgc agc tgt gtg cac      534
gga gtg tgc aac cat ggg cca cgt ggg gat gga agc tgc ctg tgc ttt      582
gct gga tac act ggc ccc cac tgt gat caa gag ctg ccc gtc tgc cag      630
gag ctg cgc tgt ccc cag aac acc cag tgc tcc gca gag gct ccc agc      678
tgc agg tgc ctg ccc ggc tac aca cag cag ggc agt gaa tgc cga gcc      726
ccc aac ccc tgc tgg cca tca ccc tgc tca ctg ctg gcc cag tgc tcg      774
gtg agc ccc aag ggg cag gct cag tgt cac tgc cct gag aac tac cat      822
ggc gat ggg atg gtg tgt ctg ccc aag gac cca tgc act gac aac ctt      870
ggt ggc tgc ccc agc aac tct act ttg tgt gtg tac cag aag ccg ggc      918
cag gcc ttc tgc acc tgc cgg cca ggc ctg gtc agc atc aac agc aac      966
gct tct gcg ggc tgc ttc gcc ttc tgc tcc ccc ttc tcc tgc gac cgg     1014
tct gcc act tgc cag gtg acc gct gat ggg aag acc agc tgt gtg tgc     1062
agg gaa agc gag gtg ggg gat ggg cgt gcc tgc tac gga cac ctg ctc     1110
cac gag gtg cag aag gcc acg cag aca ggc cgg gtg ttc ctg cag ctg     1158
agg gtc gcc gtg gcc atg atg gac cag ggc tgc cgg gaa atc ctt acc     1206
aca gcg ggc cct ttc acc gtg ctg gtg cca tcc gtc tcc tcc ttc tcc     1254
tcc agg acc atg aat gca tcc ctt gcc cag cag ctc tgt aga cag cac     1302
atc atc gca ggg cag cac atc ctg gag gac aca agg acc caa caa aca     1350
cga agg tgg tgg acg ctg ccc ggg cag gag atc acc gtc acc ttt aac     1398
caa ttc acg aaa tac tcc tac aag tac aaa gac cag ccc cag cag acg     1446
ttc aac atc tac aag gcc aac aac ata gca gct aat ggc gtc ttc cac     1494
gtg gtc act ggc ctg cgg tgg cag gcc ccc tct ggg acc cct ggg gat     1542
ccc aag aga act atc gga cag atc ctc gcc tct acc gag gcc ttc agc     1590
cgc ttt gaa acc atc ctg gag aac tgt ggg ctg ccc tcc atc ctg gac     1638
gga cct ggg ccc ttc aca gtc ttt gcc cca agc aat gag gct gtg gac     1686
agc ttg cgt gac ggc cgc ctg atc tac ctc ttc aca gcg ggt ctc tct     1734
aaa ctg cag gag ttg gtg cgg tac cac atc tac aac cac ggc cag ctg     1782
acc gtt gag aag ctc atc tcc aag ggt cgg atc ctc acc atg gcg aac     1830
cag gtc ctg gct gtg aac att tct gag gag ggg cgc atc ctg ctg gga     1878
ccc gag ggg gtc ccg ctg cag agg gta gac gtg atg gcc gcc aat ggt     1926
gtg atc cac atg ctg gac ggc atc ctg ctg ccc ggc atc ctg ccc     1974
atc ctg ccc aag cac tgc agc gag gag cag cac aag att gtg gcg ggc     2022
tcc tgt gtg gac tgc caa gcc ctg aac acc agc acg tgt ccc ccc aac     2070
agt gtg aag ctg gac atc ttc ccc aag gag tgt gtc tac atc cat gac     2118
cca acg ggg ctc aat gtg cta aag aag ggc tgt gcc agc tac tgc aac     2166
caa acc atc atg gaa caa ggc tgc tgc aaa ggt ttt ttc ggg cct gac     2214
tgc acg cag tgt cct ggg ggc ttc tcc aac ccc tgc tat ggc aaa ggc     2262
aat tgc agt gat ggg atc cag ggc aat ggg gcc tgc ctc tgc ttc cca     2310
gac tac aag ggc atc gcc tgc cac atc tgc tcg aac cca aac aag cat     2358
```

*Fig. 9*

```
gga gag caa tgc cag gaa gac tgc ggc tgt gtc cat ggt ctc tgc gac    2406
aac cgc cca ggc agt ggg ggg gtg tgc cag cag ggc acg tgt gcc cct    2454
ggc ttc agt ggc cgg ttc tgc aac gag tcc atg ggg gac tgt ggg ccc    2502
aca ggg ctg gcc cag cac tgc cac ctg cat gcc cgc tgt gtt agc cag    2550
gag ggt gtt gcc aga tgt cgc tgt ctt gat ggc ttt gag ggt gat ggc    2598
ttc tcc tgc aca cct agc aac ccc tgc tcc cac ccg gac cgt gga ggc    2646
tgc tca gag aat gct gag tgt gtc cct ggg tcc ctg ggc acc cac cac    2694
tgc aca tgc cac aaa ggc tgg agt ggg gat ggc cgc gtc tgt gtg gct    2742
att gac gag tgt gag ctg gac gtg aga ggt ggc tgc cac acc gat gcc    2790
ctc tgc agc tat gtg ggc ccc ggg cag agc cga tgc acc tgc aag ctg    2838
ggc ttt gcc ggg gat ggc tac cag tgc agc ccc atc gac ccc tgc cgg    2886
gca ggc aat ggc ggc tgc cac ggc ctg gcc acc tgc cgg gca gtg ggg    2934
gga ggt cag cgg gtc tgc acg tgc ccc cct ggc ttt ggg ggt gat ggc    2982
ttc agc tgt tat gga gac atc ttc cgg gag ctg gag gca aat gcc cac    3030
ttc tcc atc ttc tac caa tgg ctt aag agt gcc ggc atc acg ctt       3075
cct gcc gac cgc cga gtc aca gcc ctg gtg ccc tcc gag gct gca        3120
gtc cgt cag ctg agc ccc gag gac cga gct ttc tgg ctg cag cca        3165
agg acg ctg ccg aac ctg gtc agg gcc cat ttt ctc cag ggt gcc        3210
ctc ttc gag gag gag ctg gcc cgg ctg ggt ggg cag gaa gtg gcc        3255
acc ctg aac ccc acc aca cgc tgg gag att cgc aac att agt ggg        3300
agg gtc tgg gtg cag aat gcc agc gtg gat gtg gct gac ctc ctt        3345
gcc acc aac ggt gtc cta cac atc ctc agc cag gtc tta ctg ccc        3390
ccc cga ggg gat gtg ccc ggt ggg cag cgg ttg ctg cag cag ctg        3435
gac ttg gtg cct gcc ttc agc ctc ttc cgg gaa ttg ctg cag cac        3480
cat ggg ttg gtg ccc cag att gag gct gcc act gcc tac acc atc        3525
ttt gtg ccc acc aac cgc tcc ctg gag gcc cag ggc aac agc agt        3570
cac ctg gac gca gac aca gtg cgg cac cat gtg gtc ctg ggg gag        3615
gcc ctc tcc atg gaa acc ctg cgg aag ggt gga cac cgc aac tcc        3660
ctc ctg ggc cct gcc cac tgg atc gtc ttc tac aac cac agt ggc        3705
cag cct gag gtg aac cat gtg cca ctg gaa ggc ccc atg ctg gag        3750
gcc cct ggc cgc tcg ctg att ggt ctg tcg ggg gtc ctg acg gtg        3795
ggc tca agt cgc tgc ctg cat agc cac gct gag gcc ctg cgg gag        3840
aaa tgt gta aac tgc acc agg aga ttc cgc tgc act cag ggc ttc        3885
cag ctg cag gac aca ccc agg aag agc tgt gtc tac cga tct ggc        3930
ttc tcc ttc tcc cgg ggc tgc tct tac aca tgt gcc aag aag atc        3975
cag gtg ccg gac tgc tgc cct ggt ttc ttt ggc acg ctg tgt gag        4020
cca tgc cca ggg ggt cta ggg ggg gtg tgc tca ggc cat ggg cag        4065
tgc cag gac agg ttc ctg ggc agc ggg gag tgc cac tgc cac gag        4110
ggc ttc cat gga acg gcc tgt gag gtg tgt gag ctg ggc cgc tac        4155
ggg ccc aac tgc acc gga gtg tgt gac tgt gcc cat ggg ctg tgc        4200
cag gag ggg ctg caa ggg gac gga agc tgt gtc tgt aac gtg ggc        4245
tgg cag ggc ctc cgc tgt gac cag aaa atc acc agc cct cag tgc        4290
cct agg aag tgc gac ccc aat gcc aac tgc gtg cag gac tcg gcc        4335
gga gcc tcc acc tgc gcc tgt gct gcg gga tac tcc ggc aat ggc        4380
atc ttc tgt tca gag gtg gag ccc tgc gcc cac ggc cat gtt ggc        4425
tgc tcc cct cat gcc aac tgt acc aag gtg gca cct ggg cag cgg        4470
aca tgc acc tgc cag gat ggc tac atg ggc gac ggg gag ctg tgc        4515
cag gaa att aac agc tgt ctc atc cac cac ggg gcc tgc cac att        4560
cac gcc gag tgc atc ccc act ggc ccc cag cag gtc tcc tgc agc        4605
tgc cgt gag ggt tac agc ggg gat ggc atc cgg acc tgc gag ctc        4650
ctg gac ccc tgc tct aag aac aat gga gga tgc agc cca tat gcc        4695
```

*Fig. 9 (cont.)*

```
acc tgc aaa agc aca  ggg gat ggc cag agg  aca tgt acc tgc gac        4740
aca gcc cac acc gtg  ggg gac ggc ctc acc  tgc cgt gcc cga gtc        4785
ggc ctg gag ctc ctg  agg gat aag cat gcc  tca ttc ttc agc ctc        4830
cgc ctc ctg gaa tat  aag gag ctc aag ggc  gat ggg cct ttc acc        4875
atc ttc gtg ccg cac  gca gat cta atg agc  aac ctg tcg cag gat        4920
gag ctg gcc cgg att  cgt gcg cat cgc cag  ctg gtg ttt cgc tac        4965
cac gtg gtt ggc tgt  cgg cgg ctg cgg agc  gag gac ctg ctg gag        5010
cag ggg tac gcc acg  gcc ctc tca ggg cac  cca ctg cgc ttc agc        5055
gag agg gag ggc agc  ata tac ctc aat gac  ttc gcg cgc gtg gtg        5100
agc agc gac cat gag  gcc gtg aac ggc atc  ctg cac ttc att gac        5145
cgt gtc ctg ctg ccc  ccc gag gcg ctg cac  tgg gag cct gat gat        5190
gct ccc atc ccg agg  aga aat gtc acc gcc  gcc gcc cag ggc ttc        5235
ggt tac aag atc ttc  agc ggc ctc ctg aag  gtg gcc ggc ctc ctg        5280
ccc ctg ctt cga gag  gca tcc cat agg ccc  ttc aca atg ctg tgg        5325
ccc aca gac gcc gcc  ttt cga gct ctg cct  ccg gat cgc cag gcc        5370
tgg ctg tac cat gag  gac cac cgt gac aag  cta gca gcc att ctg        5415
cgg ggc cac atg att  cgc aat gtc gag gcc  ttg gca tct gac ctg        5460
ccc aac ctg ggc cca  ctt cga acc atg cat  ggg acc ccc atc tct        5505
ttc tcc tgc agc cga  acg cgg ccc ggt gag  ctc atg gtg ggt gag        5550
gat gat gct cgc att  gtg cag cgg cac ttg  ccc ttt gag ggt ggc        5595
ctg gcc tat ggc atc  gac cag ctg ctg gag  cca cct ggc ctt ggt        5640
gct cgc tgt gac cac  ttt gag acc cgg ccc  ctg cga ctg aac acc        5685
tgc agc atc tgt ggg  ctg gag cca ccc tgt  cct gag ggg tca cag        5730
gag cag ggc agc cct  gag gcc tgc tgg cgc  ttc tac ccg aag ttc        5775
tgg acg tcc cct ccg  ctg cac tct ttg gga  tta cgc agc gtc tgg        5820
gtc cac ccc agc ctt  tgg ggt agg ccc caa  ggc ctg ggc agg ggc        5865
tgc cac cgc aat tgt  gtc acc acc acc tgg  aag ccc agc tgc tgc        5910
cct ggt cac tat ggc  agt gag tgc caa gct  tgc cct ggc ggc ccc        5955
agc agc cct tgt agt  gac cgt ggc gtg tgc  atg gac ggc atg agt        6000
ggc agt ggg cag tgt  ctg tgc cgt tca ggt  ttt gct ggg aca gcc        6045
tgt gaa ctc tgt gct  cct ggt gcc ttt ggg  ccc cat tgt caa gcc        6090
tgc cgc tgc act gtg  cat ggc cgc tgt gat  gag ggc ctt ggg ggc        6135
tct ggc tcc tgc ttc  tgt gat gaa ggc tgg  act ggg cca cgc tgt        6180
gag gtg caa ctg gag  ctg cag cct gtg tgt  acc cca ccc tgt gca        6225
ccc gag gct gtg tgc  cgt gca ggc aac agc  tgt gag tgc agc ctg        6270
ggc tat gaa ggg gat  ggc cgc gtg tgt aca  gtg gca gac ctg tgc        6315
cag gac ggg cat ggt  ggc tgc agt gag cac  gcc aac tgt agc cag        6360
gta gga aca atg gtc  act tgt acc tgc ctg  ccc gac tac gag ggt        6405
gat ggc tgg agc tgc  cgg gcc cgc aac ccc  tgc aca gat ggc cac        6450
cgc ggg ggc tgc agc  gag cac gcc aac tgc  ttg agc acc ggc ctg        6495
aac aca cgg cgc tgt  gag tgc cac gca ggc  tac gta ggc gat gga        6540
ctg cag tgt ctg gag  gag tcg gaa cca cct  gtg gac cgc tgc ttg        6585
ggc cag cca ccg ccc  tgc cac tca gat gcc  atg tgc act gac ctg        6630
cac ttc cag gag aaa  cgg gct ggc gtt ttc  cac ctc cag gcc acc        6675
agc ggc cct tat ggt  ctg aac ttt cgg gag  gct gag gcg gca tgc        6720
gaa gca cag gga gcc  gtc ctt gct tca ttc  cct cag ctc tct gct        6765
gcc cag cag ctg ggc  ttc cac ctg tgc ctc  atg ggc tgg ctg gcc        6810
aat ggc tcc act gcc  cac cct gtg gtt ttc  cct gtg gcg gac tgt        6855
ggc aat ggt cgg gtg  ggc gta gtc agc ctg  ggt gcc cgc aag aac        6900
ctc tca gaa cgc tgg  gat gcc tac tgc ttc  cgt gtg caa gat gtg        6945
gcc tgc cga tgc cga  aat ggc ttc gtg ggt  gac ggg atc agc acg        6990
```

*Fig. 9 (cont.)*

```
tgc aat ggg aag ctg    ctg gat gtg ctg gct    gcc act gcc aac ttc         7035
tcc acc ttc tat ggg    atg cta ttg ggc tat    gcc aat gcc acc cag         7080
cgg ggt ctc gac ttc    ctg gac ttc ctg gat    gat gag ctc acg tat         7125
aag aca ctc ttc gtc    cct gtc aat gaa ggc    ttt gtg gac aac atg         7170
acg ctg agt ggc cca    gac ttg gag ctg cat    gcc tcc aac gcc acc         7215
ctc cta agt gcc aac    gcc agc cag ggg aag    ttg ctt ccg gcc cac         7260
tca ggc ctc agc ctc    atc atc agt gac gca    ggc cct gac aac agt         7305
tcc tgg gcc cct gtg    gcc cca ggg aca gtt    gtg gtt agc cgt atc         7350
att gtg tgg gac atc    atg gcc ttc aat ggc    atc atc cat gct ctg         7395
gcc agc ccc ctc ctg    gca ccc cca cag ccc    cag gca gtg ctg gcg         7440
cct gaa gcc cca cct    gtg gcg gca ggc gtg    ggg gct gtg ctt gcc         7485
gct gga gca ctg ctt    ggc ttg gtg gcc gga    gct ctc tac ctc cgt         7530
gcc cga ggc aag ccc    acg ggc ttt ggc ttc    tct gcc ttc cag gcg         7575
gaa gat gat gct gac    gac gac ttc tca ccg    tgg caa gaa ggg acc         7620
aac ccc acc ctg gtc    tct gtc ccc aac cct    gtc ttt ggc agc gac         7665
acc ttt tgt gaa ccc    ttc gat gac tca ctg    ctg gag gag gac ttc         7710
cct gac acc cag agg    atc ctc aca gtc aag    tgacgaggct ggggctgaaa       7760
gcagaagcat gcacagggag gagaccactt ttattgcttg tctgggtgga tggggcagga         7820
ggggctgagg gcctgtccca gacaataaag tgccctcagc ggatgtgggc catgtcacc         7879
```

Fig. 9 (cont.)

COMMON LYMPHATIC ENDOTHELIAL AND VASCULAR ENDOTHELIAL RECEPTOR-1 (CLEVER-1) AND USES THEREOF

BACKGROUND OF THE INVENTION

1. Field of the Invention

The invention is in the field of cell adhesion proteins. Specifically, the invention is in the field of CLEVER-1, a novel protein that facilitates the influx of leukocytes and malignant cells into the lymphatic system, and also the efflux of the same out of the lymph nodes.

2. Background Art

Leukocytes are the major cellular components of inflammatory and immune responses. Leukocytes include lymphocytes, natural killer (NK) cells, monocytes, dendritic cells and granulocytes (neutrophils, eosinophils and basophils). See, HARRISON'S PRINCIPLES OF INTERNAL MEDICINE, Fauci, A. S. et al. eds. (14th ed. 1998). Lymphocytes are composed of B cells and T cells. B cells provide humoral immunity and are the precursors of plasma cells. T cells provide cell mediated immunity. In tissues monocytes differentiate further into macrophages. At sites of inflammation, blood monocytes can attach to inflamed endothelia. Macrophages recognize and take up a wide range of exogenous materials such as bacteria. Granulocytes also have critical roles in inflammation. They are needed to clear infections with extracellular bacteria. The immune response has an important role in the growth, differentiation, and mobilization of granulocytes.

Continuous lymphocyte recirculation between blood and lymphoid tissues forms a basis for the function of the immune system. However such lymphocyte recirculation inadvertently also facilitates at least two medical conditions: inflammation and metastasis.

Lymphocytes enter the lymphoid tissues by binding to vascular endothelial cells. Lymphocyte adherence to endothelial cells is mediated by complementary, surface expressed molecules on both cell types. The adhesion molecules and mechanisms of lymphocyte entrance into the tissues from the blood have been thoroughly characterized, but mechanisms controlling lymphocyte exit from the non-lymphoid and lymphoid tissues via lymphatics have remained unknown.

The majority of lymphocytes extravasate into the lymph nodes via specialized vessels called high endothelial venules, or HEV. The rest of the incoming lymphocytes enter the nodes via afferent lymphatics together with antigens and other types of hematopoietic cells such as dendritic cells, macrophages and granulocytes. However, only lymphocytes are able to leave the nodes via the efferent lymphatic system by first traversing the sinusoidal endothelium and then entering the efferent lymphatic vessel. To maintain the homeostasis in the lymph node the numbers of entering and exiting lymphocytes need to be well balanced. The molecular mechanisms involved in lymphocyte exit are unknown.

In addition to being of fundamental importance in normal lymphocyte recirculation, the lymphatics also regulate seeding of metastasizing cells in approximately 50% of cancers that use this type of vessel for spreading. Lymph nodes are often the first organ to develop metastases, especially in the case of carcinomas. The design of the lymphatic system makes it relatively easy for malignant tumor cells to enter (Sleeman, J. P., *Recent Results Cancer Res.* 157:55-81 (2000)), and thus compounds that prevent the entry and exit of malignant tumor cells from the lymphatics have tremendous therapeutic potential.

BRIEF SUMMARY OF THE INVENTION

Recognizing the need to control lymphocyte recirculation, the inventors initiated a study of the proteins of the efferent lymphatic vessels. These studies have culminated in the discovery of a novel protein, Common Lymphatic Endothelial and Vascular Endothelial Receptor-1 (CLEVER-1), a binding protein that mediates adhesion of lymphocytes (and malignant tumor cells) to endothelium in both the systemic vasculature and in the lymphatics. The inventors have discovered that by blocking the interaction of CLEVER-1 and its lymphocyte substrate, the artisan can, for the first time simultaneously, control lymphocyte recirculation and lymphocyte migration, and related conditions such as inflammation, at the site of lymphocyte influx into, and efflux from, the tissues. The inventors have also discovered that CLEVER-1 also mediates binding of other types of leukocytes such as monocytes and granulocytes to HEV-like vessels. Further, by blocking the interaction of CLEVER-1 and malignant tumor cells, the artisan can also, for the first time, control metastasis by preventing malignant cells that bind to CLEVER-1 from being taken up by the lymphatic vessels, and thus preventing spread of the malignancy into the lymph nodes.

Accordingly, in a first embodiment, the invention is directed to cellular and subcellular extracts that contain CLEVER-1.

In a further embodiment, the invention is directed to purified or isolated CLEVER-1.

The invention further provides a method for inhibiting CLEVER-1 mediated leukocyte (such as lymphocyte, monocyte, and granulocyte) adhesion in a subject in need of the same, such method comprising administering a CLEVER-1 binding agent, or soluble CLEVER-1, to such subject.

The invention further provides a method for preventing or reducing CLEVER-1 mediated inflammation in a subject in need of the same, such method comprising administering a CLEVER-1 binding agent, or soluble CLEVER-1, to such subject.

The invention further provides a method for inhibiting CLEVER-1 mediated metastasis of malignant cells in a subject in need of the same, especially metastasis into the lymph nodes, such method comprising blocking the interaction of CLEVER-1 and the metastasizing cell in such subject with a CLEVER-1 binding agent, or by administering soluble CLEVER-1, to such subject.

The invention further provides a method for extracting cells that bind to CLEVER-1 from a population of cells, such method comprising mixing a population of cells with a preparation that contains CLEVER-1 and purifying the CLEVER-1-cell complex away from the rest of the non-binding cells in the population. Such method can be used to enrich for a subpopulation of CLEVER-1 binding cells.

The invention further provides a method for identifying an agent that binds to CLEVER-1, such method comprising determining whether a substance will successfully or unsuccessfully compete with leukocytes, malignant cells or with CLEVER-1 antibodies for binding to CLEVER-1.

The invention further provides a method for identifying an agent that is capable of inhibiting CLEVER-1 mediated cell migration, such method comprising assaying CLEVER-1 trafficking of lymphocytes into the afferent lymphatics or HEV, and/or out of the lymph nodes, in the presence of such agent, and identifying such agent on the basis of its ability to inhibit such trafficking. In another embodiment, CLEVER-1 trafficking of malignant cells is assayed.

The present invention also provides a method of stimulating CLEVER-1 binding, for example, in immunocompromised hosts to facilitate leukocyte (such as lymphocyte, monocyte and granulocyte) trafficking and the function of immune defense systems.

BRIEF DESCRIPTION OF THE DRAWINGS

FIGS. 1a-1c are from the skin, FIGS. 1d-1i are from a lymph node. FIGS. 1a, 1d and 1g show the staining with monoclonal antibody 3-266, FIGS. 1b, 1e and 1h show the staining with monoclonal antibody 3-372 and FIGS. 1c, 1f and 1i show the staining with a negative control antibody, 3G6. In FIGS. 1a, 1b and 1c, the arrows point to the epithelium and arrowheads to afferent lymphatics. In FIGS. 1d and 1e, the arrows point to the lymphatic vessles (lymphatic sinusoids that belong to the efferent lymphatic system) within the lymph node. In FIGS. 1g and 1h, the arrows point to HEV.

FIG. 2. Monoclonal antibodies 3-266 and 3-372 recognize an about 270-300 kDa molecule. Molecules in lymph node lysates were separated by SDS-PAGE, blotted to nitrocellulose sheets and probed with monoclonal antibody 3-266 and 3-372 or with a negative control antibody (3G6).

FIGS. 5d-5f, skin). FIG. 5a. Fibrotic type of inflamed synovium without any marked infiltrations of inflammatory cells. Only the afferent lymphatics expressed CLEVER-1 (arrows). FIG. 5b. CLEVER-1 was upregulated on a HEV-like vessel (marked by a dashed line) within a heavy lymphocytic infiltration. FIG. 5c. Staining with a negative control antibody (3G6). FIG. 5d. In normal skin afferent lymphatics expressed CLEVER-1 (arrows), but in inflamed skin HEV-like vessels (dashed line) also expressed CLEVER-1 (FIG. 5e). Negative control staining (FIG. 5f). Arrowheads point to epidermis (FIGS. 5d-5f).

FIG. 9. The nucleotide sequence (7879 nt) of CLEVER-1 (SEQ ID NO:1). Boxed in grey are the translation initiation codon, translation stop codon, the two RGDs, the potential polyadenylation signal and the four nucleotide differences compared to Genebank entry AJ 2752213 (stabilin-1), i.e., nucleotides 1131, 2767, 6629 and 6969. Underlined are the nucleotides corresponding to the alternatively spliced exons.

DETAILED DESCRIPTION OF THE INVENTION

Figure 1:
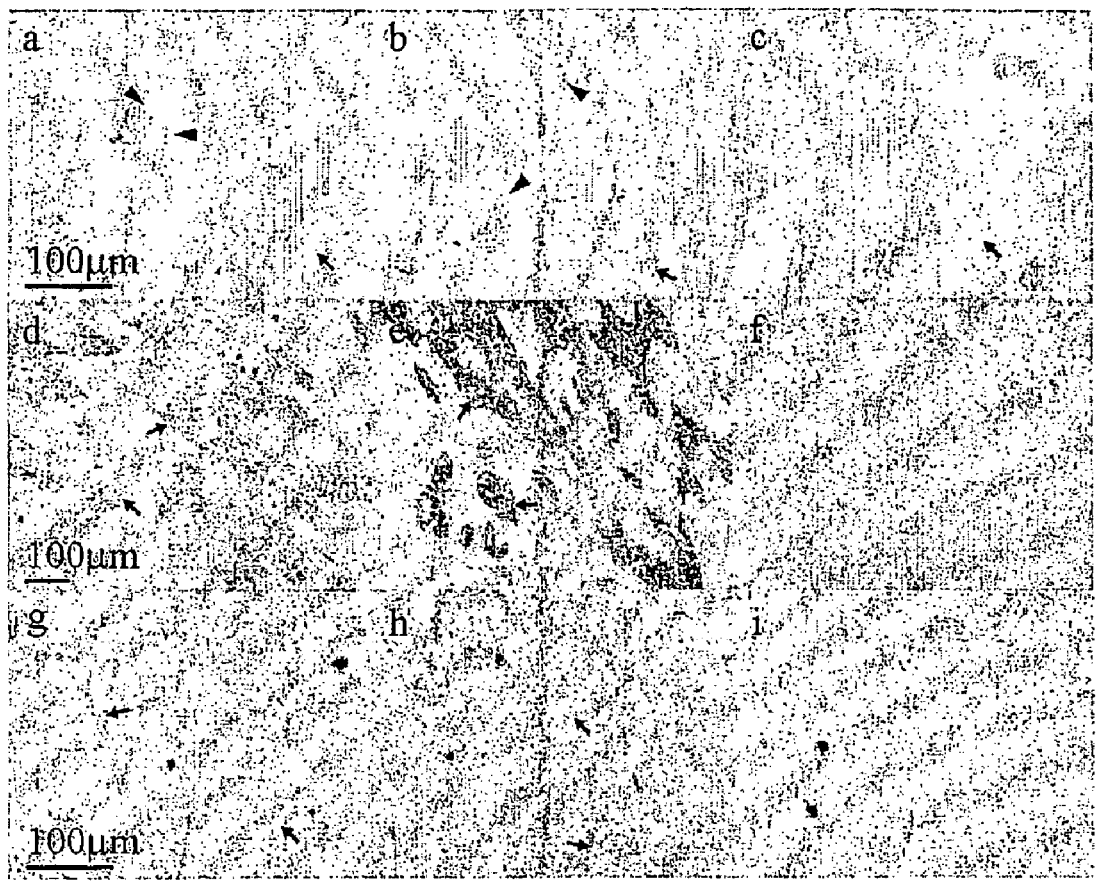
FIGS. 1a-1i. Indirect immunoperoxidase staining showing that monoclonal antibodies 3-266 and 3-372 recognize endothelium both in afferent and efferent lymphatic systems and on HEV.

The term "ameliorate" denotes a lessening of an effect. To ameliorate a condition or disease refers to a lessening of the symptoms of the condition or disease.

The term "modulate" means to control in a predictable fashion, either by increasing or by decreasing the targeted parameter, as indicated from the context.

The term "effective amount" refers to that amount of the indicated agent that is sufficient to achieve the desired effect.

The term "inflammatory condition" refers to a physiological or pathological condition that is accompanied by an inflammatory response in a subject, which includes, inter alia, an undesired accumulation of leukocytes at one or more sites in such subject. The inflammatory condition can be hyperacute, acute, subacute or chronic. The inflammatory condition can be localized at the site of the inflammatory lesion or diffuse throughout the subject.

The term "drug" denotes any pharmaceutical or physiological agent, composition, bioactive compound, or combinations thereof, useful in the diagnosis, cure, mitigation, treatment, or prevention of a disease, or for any other medical purpose. The term "drug" is intended to be interpreted broadly and is not limited in terms of chemical composition or biological activity.

The term "essentially free of contaminants" refers to a substance that is of, undesired or unnecessary substances that had been present during the in vitro or in vivo synthesis of the desired substance.

The term "treatment" or "treating" refers to the administration of an agent to a subject for purposes which can include prophylaxis, amelioration, prevention or cure of an undesired disorder. Such treatment need not necessarily completely ameliorate the disorder, for example, inflammation; it is sufficient that such treatment ameliorates the disorder to a degree that is beneficial to the subject to which it is administered. Further, such treatment can be used in conjunction with other traditional treatments, for example, alternative treatments for reducing the inflammatory condition, known to those of skill in the art and as desired by the practitioner.

By "systemic vasculature" is meant the vascular network of blood vessels throughout the body of an animal or human.

By "lymphatic system" is meant the specialized part of the circulatory system that consists of lymph, the lymphatics, and the lymph nodes. The lymph nodes are located along the paths of the lymph collecting vessels and in isolated nodules of lymphatic patches in the intestinal wall. Additionally, there are specialized lymphatic organs such as the tonsils, thymus and spleen. B lymphocytes begin their final stages of maturation within the germinal centers of the lymph nodes' cortical nodules. Maturing lymphocytes are then pushed to the more densely packed outer layers as they mature, before being released into the efferent lymphatics. The lymph nodes that are located in the floor of the mouth are called the submental and submaxillary lymph nodes. The superficial cervical lymph nodes are located in the neck. The superficial cubital or supratroclear lymph nodes are located just above the bend in the elbow. The axillary lymph nodes are clustered deep within the underarm and upper chest region. Inguinal lymph nodes are located in the groin. By "lymphatics" is meant the vessels that return lymph to the blood. Lymph is the clear fluid that flow in the lymphatics. Lymph arises from plasma that filters into the interstitial spaces from blood flowing through the capillaries. Although most of this plasma is taken up and absorbed by cells or the blood, a small amount is not absorbed. The lymphatics act as drains to collect this excess fluid and return it to the venous blood just before it reaches the heart. The lymph nodes act as filters that collect the lymph from several different lymphatics and "percolate" the lymph through spaces termed sinuses before draining into a single efferent draining vessel.

By "afferent lymphatics" is meant the vessels through which antigens enter the lymph nodes. Lymphocytes can enter the lymph nodes via the afferent lymphatics or via the high endothelial venules (HEV).

By "high endothelial venules" (HEV) is meant a specialized cortical postcapillary venules whose endothelium is simple cuboidal to columnar instead of simple squamous. HEVs are located mainly in the paracortex of the lymph nodes. Lymphocytes cross the HEV, and thus "traffic" into the lymph nodes by diapedesis, that is, the lymphocytes stick to the luminal surface of the HEV, and then squeeze into the space between two or more HEV cells.

By "efferent lymphatics" meant the vessels that drain the lymph nodules (nodes).

By "lymphocyte recirculation" is meant the continuous movement of lymphocytes throughout the circulatory and lymph system. Lymphocytes leave the lymph node and are first delivered via the lymph to venous system draining into the heart.

The lymphocytes then circulate throughout the body in the blood-stream. Most of the lymphocytes are redelivered to the spleen or to another lymph node. About 10% go to non-lymphoid organs. Lymphocytes that have never been activated cannot enter non-lymphoid organs.

Lymphocyte "trafficking" refers to lymphocyte cell movement to specific locations. Outside of the lymph nodes, the trafficking of circulating lymphocytes allows the lymphocyte to accumulate at sites of inflammation. Activated effector lymphocytes tend to home to areas of inflammation, resulting in a large influx of lymphocytes in areas of inflammation. At the inflamed site, lymphocytes attach to the endothelial cells that line the blood vessels. This attachment localizes the lymphocyte at the site of inflammation and allows for subsequent emigration of the cells into the surrounding tissues (extravasation).

The Identification and Purification of CLEVER-1

The basis of the invention is the discovery of a new molecule, a novel protein herein designated "Common Lymphatic Endothelial and Vascular Endothelial Receptor-1 in the systemic vasculature, and in the afferent and efferent lymphatics. It has been found that leukocytes such as lymphocytes, monocytes, and granulocytes, and malignant cells specifically bind to this protein. It has also been found that this protein acts as a receptor that facilitates entry of bound leukocytes and malignant cells through the walls of the systemic vasculature, into the lymph nodes and out of the lymph nodes.

To search for a protein that played a role in lymphocyte lymphatic efflux, the inventors first identified cell migration-associated lymphatic structures from isolated efferent lymphatic vessels of human lymph nodes. These structures were used to produce monoclonal antibodies. Hybridomas were screened on frozen sections of human lymph nodes using immunoperoxidase staining.

Two of the hybridomas produced antibodies (designated 3-266 and 3-372) tat clearly stained lymphatic endothelium both in afferent and efferent lymphatic systems and vascular endothelium on HEV, while other structures remained unstained. This is consistent with the expected pattern for an antibody that recognizes a lymphocyte migration-associated structure. Cell culture of 3-266 (DSM ACC2519) and cell culture of 3-372 (DSM ACC2590) were both deposited under the terms of the Budapest Treaty on the International Recognition of the Deposit of Micro-organisms for the Purposes of Patent Procedure on Aug. 21, 2001, with DSMZ-Deutsche Sammlung von Mikroorganismen und Zelikulturen GmbH, Mascheroder Weg 1b, D-38124 Braunschweig.

In molecular weight determinations by immunoblotting, both anti-bodies recognized a molecule of the same size, about 270-300 kDa. Due to this and an identical staining pattern, these antibodies were considered to recognize the same antigen; that antigen was named Common Lymphatic Endothelial and Vascular Endothelial Receptor-1 (CLEVER-1).

CLEVER-1 was purified from CLEVER-1 containing lymph node preparations using affinity chromatography with the 3-372 antibody. The eluted material was subjected to SDS-PAGE analysis and silver staining. The specific band was excised, reduced, alkylated and digested with trypsin.

After cleavage with trypsin, mass spectrometric analyses yielded 27 peptides. Twenty-one (77%) of those had identical sequences with stabilin. These sequences covered altogether 268 amino acids (10% of the 2570 amino acids of stabilin-1) and spanned the amino acids between 53 and 2301 (Table 1). The peptide data suggest that CLEVER-1 has some homology with stabilin-i at the structural level. No functional information regarding stabilin-1 can be found in the literature.

Peptide analysis of CLEVER-1 indicates no significant homology with any of the known endothelial homing-associated molecules, such as ICAM-1 (Intercellular Adhesion Molecule), ICAM-2, or VAP-1 (Vascular Adhesion Protein).

CLEVER-1 has several structural motifs that are associated with adhesive functions in other molecules. They include a proteoglycan link homology region important in CD44 for hyaluronan binding and two RGD motifs known to serve as integrin ligands in certain molecules, such as in fibornectin. In addition, CLEVER-1 has seven fasciclin domains also present in several molecules such as priostin, fasciclin and transforming growth factor-β-induced gene, big-h3 and in all of these cases it is essential for adhesive function of these molecules. Interestingly, twenty-two epidermal growth factor (EGF) repeats are also found in CLEVER-1. This structural domain is also present in all members of the selectin family. Although the lectin domains of selectins are of utmost importance for the transient interaction with their sialomucin ligands, EGF-repeats have been reported to functionally contribute with lectin domains to binding between leukocytes and endothelium. Based on the structural complexity of CLEVER-1 it may turn out have several ligand molecules and be multifunctional in its nature.

It has been discovered that CLEVER-1 is involved in the process of lymphocyte recirculation. CLEVER-1 is present on the endothelium of the systemic vasculature, especially on the HEV and also on the endothelium of both afferent and efferent lymphatic systems. CLEVER-1 is a protein adhesion molecule, and especially, a cell adhesion molecule (CAM), that mediates adhesion of lymphocytes and of malignant tumor cells to CLEVER-1 in the systemic vasculature and the lymphatic system. These sites are of utmost importance as control points in lymphocyte trafficking.

CLEVER-1 is the first molecule that has been identified to facilitate lymphocyte and malignant cell exit from the lymph nodes. Additionally, CLEVER-1 is the first molecule that has been identified that regulates both entrance of lymphocytes and tumor cells into the lymph nodes and exit of lymphocytes and tumor cells from the lymph nodes. CLEVER-1 has been found to also mediate binding of other leukocytes such as monocytes and granulocytes to HEV-like vessels.

By "CLEVER-1 mediated cell binding" is meant the specific association of CLEVER-1 with either a leukocyte, such as a lymphocyte, monocyte, or granulocyte, or a CLEVER-1-binding malignant cell. CLEVER-1 mediated cell binding can occur with CLEVER-1 in a soluble form or in a particulate form (for example, when CLEVER-1 is present in a form that is membrane associated).

CLEVER-1 Mediated Binding of Leukocytes

According to the invention, adhesion of leukocytes, such as lymphocytes, monocytes, and granulocytes, to the endothelium (that is, to an endothelial cell(s)) in the systemic vasculature, especially the HEV, and to the endothelium in the afferent and efferent lymphatics can be blocked by blocking the binding between such endothelial cell's CLEVER-1 and leukocyte.

In the systemic vasculature, inhibiting or preventing endothelial cell CLEVER-1 mediated lymphocyte binding will inhibit or prevent lymphocytes, especially activated lymphocytes, from accumulating at such sites, and thus prevent or lessen inflammation at such sites. Thus, the invention provides a method of treating inflammation, by administering an agent that inhibits or prevents CLEVER-1 mediated endothelial cell binding to lymphocytes.

In the afferent lymphatics, inhibiting or preventing lymphocytes from binding to endothelial cell CLEVER-1 will inhibit or prevent such lymphocytes from entering the afferent lymphatics and thus the lymph nodes. Thus, the invention provides a method of treating inflammation, by administering an agent that inhibits or prevents CLEVER-1 mediated endothelial cell binding to lymphocytes in the afferent lymphatics and especially at HEV in lymph nodes or HEV-like venules at sites of inflammation. The invention also provides a method of inhibiting lymphocyte trafficking into the lymph nodes, by administering an agent that inhibits or prevents afferent lymphatic CLEVER-1 mediated endothelial cell binding, and especially HEV binding, to lymphocytes and other leukocytes.

In the efferent lymphatics, inhibiting or preventing lymphocytes from binding to endothelial cell CLEVER-1 will prevent the lymphocytes from exiting the lymph node and entering the blood. Thus, the invention provides a method of treating inflammation, by administering an agent that inhibits or prevents CLEVER-1 mediated endothelial cell binding to lymphocytes in the efferent lymphatics. The invention also provides a method of inhibiting lymphocyte trafficking out of the lymph nodes, by administering an agent that inhibits or prevents efferent lymphatic CLEVER-1 mediated endothelial cell binding to lymphocytes.

Therefore, CLEVER-1 binding with lymphocytes presents a unique, three-prong approach to treat diseases or conditions characterized by an undesired lymphocyte accumulation or trafficking in which the artisan can target lymphocyte entry into the lymph nodes, lymphocyte exit from the lymph nodes, and lymphocyte binding to the systemic vasculature, with the same agent.

The discovery of CLEVER-1 and its role has thus resulted in a new method to control lymphocyte migration by inhibiting CLEVER-1 mediated cell binding to such cells. Thus, the present invention provides a method of inhibiting undesired CLEVER-1 mediated lymphocyte trafficking, and thus blocking harmful or otherwise undesired lymphocyte migration, by preventing the association of CLEVER-1 with lymphocytes. Similarly, the invention provides a method of inhibiting undesired CLEVER-1 mediated binding of other leukocytes by preventing association of CLEVER-1 with the leukocytes.

The present invention also provides a method of stimulating CLEVER-1 binding, for example, in immunocompromised hosts to facilitate lymphocyte trafficking and other leukocyte binding and the function of immune defense systems.

CLEVER-1 Mediated Cell Binding to Malignant Cells

Because cancer cells often break away from a malignant tumor and enter the lymphatics, cancer cells travel to and establish themselves in the lymph nodes. According to the invention, the ability of a malignant tumor cell to establish itself in a lymph node can be inhibited or prevented by inhibiting or preventing CLEVER-1 binding to such malignant tumor cell.

The term "tumor" refers to a neoplasm, a tissue mass that is characteristic of a neoplasia. Neoplasia is distinguished from other forms of tissue growth, first, by the formation of a tissue mass, a neoplasm, or tumor. Second, neoplasia is considered to be an irreversible process. Third, neoplastic tissue tends to morphologically resemble its tissue of origin. Fourth, neoplastic tissue tends to functionally resemble its tissue of origin. Fifth, neoplasms grow and function somewhat independently of the homeostatic mechanisms that control normal tissue growth and function.

A neoplasm can be benign or malignant. A benign neoplasm consists of a discrete tissue mass that continues to grow. A benign neoplasm will simply push adjacent tissues out of its way as it grows.

The definitive features of a malignant neoplasm, a malignancy, are invasion and metastasis, that is, the spread of the neoplasm to a distant site. A malignant neoplasm will grow into the adjacent tissue, rather than pushing it away. The terms "malignant neoplasm," "malignant tumor," and "cancer" are synonymous.

Cancer cells typically invade thin-walled vessels such as small veins, venules, capillaries and lymphatics. The passage of cancer cells via lymphatics to lymph nodes, and via blood vessels to other organs and structures, and the subsequent implantation and growth of the cancer cells in those sites is referred to as "metastasis." The lymph nodes are common sites for metastasis.

Cancer cells can also spread by seeding—shedding into, for example, the peritoneal fluid. The cells can be carried by the fluid to a distant site on the peritoneal surface where they can implant and form new foci of cancer growth.

Most neoplasms are one of four types: epithelial, non-epithelial, blastomas and teratomas. Malignant epithelial neoplasms are termed carcinomas. An adenocarcinoma is a carcinoma in which gland-like structures are present. Carcinomas can be papillary or cystic. Benign epithelial neoplasms are generally adenomas, polyps or papillomas.

Non-epithelial tumors can also be benign or malignant. They are generally named by a prefix that indicates the histologic type and a suffix. The suffix -oma generally means benign while the suffix -sarcoma means malignant. However, several malignant neoplasms have traditional names ending in -oma: for example, melanoma, hepatoma, and lymphoma.

Lymphomas are malignant neoplasms arising from cells of the lymphoid series. Blastomas and teratomas contain more than one type of tissue. Malignant teratomas are often termed teratocarcinomas.

A "leukemia" is a tumor of white blood cells that is present in the bone marrow and blood. A "lymphoma" is a tumor of white blood cells that is present in the lymph nodes and tissues.

According to the invention, the binding of CLEVER-1-binding malignant cells to the endothelium in the systemic vasculature, especially the HEV, and to the endothelium in the afferent and efferent lymphatics can be inhibited or prevented by inhibiting or preventing the binding between such endothelial cell's CLEVER-1 and such malignant cell. Thus, the invention provides a method of treating cancer, and especially, a method of preventing metastasis, by administration of an agent that inhibits or prevents CLEVER-1 mediated malignant cell binding to the endothelium.

In the systemic vasculature, inhibiting or preventing CLEVER-1 mediated cell binding will inhibit or prevent the establishment of CLEVER-1 binding malignant cells at such sites, and thus lessen or prevent metastasis of such malignant cells. Thus, the invention provides a method of treating cancer, and especially, a method for preventing metastasis of a CLEVER-1 binding malignant cell, by administering an agent that inhibits or prevents CLEVER-1 mediated endothelial cell binding to CLEVER-1-binding tumor cells in the systemic vasculature. The invention also provides a method of inhibiting metastasis, by administering an agent that inhibits or prevents systemic vasculature CLEVER-1 mediated endothelial cell binding to such malignant cells.

In the afferent lymphatics, inhibiting or preventing CLEVER-1 binding malignant cells from binding to endothelial cell CLEVER-1 will inhibit or prevent such CLEVER-1 binding malignant cell from entering and establishing in the lymph node, and thus lessen or prevent metastasis of such cell to the lymph node or thus to other sites in the body. In this context it is worth to note that a metastasizing malignant cell cannot survive long times without matrix support—a condition present for example in blood. Thus, the invention provides a method of treating cancer, and especially, a method for preventing metastasis of a CLEVER-1 binding malignant cell, by administering an agent that inhibits or prevents CLEVER-1 mediated endothelial cell binding to CLEVER-1-binding malignant cells in the afferent lymphatics and at HEV in systemic vasculature. The invention also provides a method of inhibiting metastasis, by administering an agent that inhibits or prevents afferent lymphatic CLEVER-1 mediated endothelial cell binding, and especially HEV binding, to such malignant cells.

In the efferent lymphatics, inhibiting or preventing CLEVER-1 binding malignant cells from binding to endothelial cell CLEVER-1 will inhibit or prevent such CLEVER-1 binding malignant cell from leaving the lymph node, and thus lessen or prevent metastasis of such cell from the lymph node to other sites in the body. Thus, the invention provides a method of treating cancer, and especially, a method for preventing metastasis of a CLEVER-1 binding malignant cell, by administering an agent that inhibits or prevents CLEVER-1 mediated endothelial cell binding to CLEVER-1-binding malignant cells in the efferent lymphatics. The invention also provides a method of inhibiting metastasis, by administering an agent that inhibits or prevents efferent lymphatic CLEVER-1 mediated endothelial cell binding to such malignant cells.

CLEVER-1 interaction with CLEVER-1 binding malignant cells thus presents a unique, three-prong approach to inhibit or prevent metastasis in which not only can the artisan block such malignant cells from entering into and exiting from the lymph system, but also, the artisan can block association of such malignant cell with CLEVER-1 in the vascular endothelium.

Agents that Block or Inhibit CLEVER-1 Mediated Cell Binding

Soluble CLEVER-1 and antibodies to CLEVER-1 can be provided to the host cell to block or inhibit CLEVER-1 mediated cell binding. Soluble CLEVER-1 can be used to "coat" the CLEVER-1 binding sites on the leukocyte, such as lymphocyte, monocyte, or granulocyte, or tumor cell and thus prevent the coated cell from association with the native CLEVER-1 on the HEV or afferent or efferent lymphatics.

CLEVER-1 antibodies can be administered to a patient in need of the same to coat CLEVER-1 that is present on the vascular endothelium or lymphatics, of such patient, especially the afferent lymphatics so as to prevent leukocyte or malignant cell binding to such CLEVER-1 in the patient. CLEVER-1 antibody producing cells can be administered directly to the patient so as to provide a source of the same.

Moreover, the present invention provides a method of identifying an agent that inhibits the binding of CLEVER-1 to cells by providing an agent to cells in the presence of CLEVER-1 and comparing the binding of CLEVER-1 to cells provided with the agent to binding of CLEVER-1 in the absence of the agent. Similarly, the invention provides a method of identifying an agent that stimulates the binding of CLEVER-1 to cells by providing an agent to cells in the presence of CLEVER-1 and comparing the binding of CLEVER-1 to cells provided with the agent to binding of CLEVER-1 in the absence of said agent.

The term "antibody" is used in the broadest sense and specifically covers single monoclonal antibodies (including agonist and antagonist antibodies), polyclonal antibodies, as well as antibody fragments and single chain antibodies (e.g., Fab, F(ab')$_2$, Fv), so long as they exhibit the desired biological activity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

Single chain "Fv" is the minimum antibody fragment which contains a complete antigen recognition and binding site. This region consists of a dimer of one heavy and one light chain variable domain in tight, noncovalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. See, Ladner et al., U.S. Pat. No. 4,946,778, and Bird, R. E. et al., *Science*, 242:423-426 (1988).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by a hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256:495 (1975), or may be made by recombinant DNA methods (e.g., Cabilly et al., U.S. Pat. No. 4,816,567).

Preparation of immunizing antigen, and polyclonal and monoclonal antibody production can be performed as described herein, or using other suitable techniques. A variety of methods have been described (see e.g., Kohler et al., *Nature* 256:495-497 (1975), and *Eur. J. Immunol.* 6:511-519 (1976); Milstein et al., *Nature* 266:550-552 (1977); Koprowski et al., U.S. Pat. No. 4,172,124; Harlow, E. and D. Lane, Antibodies: A Laboratory Manual (Cold Spring Harbor Laboratory: Cold Spring Harbor, N.Y., 1988); CURRENT PROTOCOLS IN MOLECULAR BIOLOGY, Vol. 2 (Supplement 27, 1994), Ausubel, F. M. et al., John Wiley & Sons, eds., New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired binding properties can be selected by a suitable assay (e.g., ELISA).

The term "antibody" also includes chimeric, humanized or primatized (CDR-grafted) antibodies, as well as chimeric or CDR-grafted single chain antibodies, and the like, comprising portions derived from different species. "Chimeric" antibodies (immunoglobulins) have a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., U.S. Pat. No. 4,816,567; Morrison et al., *Proc. Natl. Acad. Sci. USA* 81:6851-6855 (1984). The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., EP 0 125 023 B1; Boss et al., U.S. Pat. No. 4,816,397; Boss et al., EP 0120694 B1; Neuberger, M. S. et al., WO 86/01533; Neuberger, M. S. et al., EP 0194276 B1; Winter, U.S. Pat. No. 5,225,539; Winter, EP 0239400 B1; and Queen et al., U.S. Pat. Nos. 5,585,089, 5,698,761 and 5,698,762. See also, Newman, R. et al., *Bio-Technology* 10: 1455-1460 (1992), regarding primatized antibody.

By "agonist antibody" is meant an antibody which is able to bind to CLEVER-1 and facilitate adhesion of lymphocytes (and malignant tumor cells) to endothelium. By "antagonist antibody" is meant an antibody that is able to bind to CLEVER-1 and inhibit adhesion of lymphocytes (and malignant tumor cells) to endothelium.

Anti-idiotypic antibodies are also provided. Anti-idiotypic antibodies recognize antigenic determinants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880.

In Vitro Adhesion Assay and Diagnostic Uses Thereof

In a further embodiment, the present invention is directed to an adhesion assay in which CLEVER-1 binding is used to assay for the presence of leukocytes or malignant cells that bind to HEV and lymphatic endothelium. Both static and non-static assays are possible. The adhesion assay is exemplified in Example 4. Both static and non-static assays can be used to study leukocyte binding to systemic vasculature.

In the static assay, a tissue section is exposed to leukocytes or malignant cells for a desired period of time, without continuous agitation or rotation of the preparation during the exposure. Static assays are preferred for examining the ability of leukocytes and malignant cells to bind to lymphatic endothelium, especially the efferent lymph vessels.

In the non-static assay, the CLEVER-1 containing tissue sample and leukocytes are constantly rotated during the time period in which the leukocytes are given to adhere to the CLEVER-1. Non-static assays are preferred for studying leukocyte and malignant cell binding to CLEVER-1 in the HEV. The non-static assay mimics adhesion to the systemic vasculature.

In another embodiment, the present invention relates to a method for detection of malignant tumor cells. As explained with detail in Example 1, CLEVER-1 antibodies reduce the binding of malignant tumor cells to the vascular and lymphoid endothelium, demonstrating CLEVER-1 is a receptor for such malignant tumor cells. CLEVER-1 protein, or fragments thereof, or CLEVER-1 binding compounds, including but not restricted to, antibodies against CLEVER-1, both monoclonal and polyclonal, antibodies against antigenic fragments of CLEVER-1, both monoclonal and polyclonal, antigenic polypeptides, small molecule inhibitors or drugs, can be used in both quantitative and qualitative assays to detect the presence of malignant tumor cells in a sample, said sample being tissue or blood from a human or animal.

CLEVER-1 protein, or fragments thereof, or the above-mentioned CLEVER-1 binding compounds can be attached to a solid support matrix, including but not limited to microtiter plates, agarose columns, or magnetic beads. The above-mentioned sample can then be exposed to said solid support matrix, and the percentage of cells retained by said solid support matrix determined. For example, a sample from a normal, healthy individual, said individual being either a human or an animal, would have a statistically predicted number of leukocytes that bind to CLEVER-1. A sample that contains both leukocytes and malignant tumor cells would have a detectably higher number of cells that bind CLEVER-1.

In a preferred embodiment, a blood or tissue sample that has been taken from a patient who is in need of treatment, especially treatment for cancer, is used as the source of the CLEVER-1 binding cells in the in vitro adhesion assay. Such patient can be a patient being treated for a previously diagnosed malignancy, or a patient suspected of having a malignant tumor, or a patient who appears to be cured of such malignant tumor but is in need of monitoring for the reoccurrence of the same. Preferably, such blood or tissue sample is from a patient who is to be tested for the presence of malignant cells that bind to CLEVER-1 in such sample.

The blood or tissue sample that is to be examined in the in vitro assay of the invention can be processed, if desired, by methods known in the art so as to further extract or concentrate any CLEVER-1 binding cells that might be present in the sample, prior to the sample's being used in the in vitro adhesion assay of the invention.

Additionally, once the in vitro adhesion assay is complete, the adherent cells can be studied using other methods. For example, in the static assay, where the bound cells have been fixed, ability of the adherent cells to be recognized by a monoclonal antibody that is diagnostic for the type of tumor can be performed.

Detecting the binding of malignant cells to the CLEVER-1 containing lymphatic endothelium indicates that the patient is in need of treatment for such malignant cells, and especially to prevent the metastasis of such malignant cells The present invention provides in this aspect a novel, efficient, and convenient assay for identifying antagonists, including but not limited to, monoclonal and polyclonal antibodies, peptides, protein fragments, small molecular inhibitors, drugs, and other agents, which can inhibit the adhesion of leukocytes and malignant tumor cells to the vascular and lymphatic endothelium.

For example, CLEVER-1 containing samples of lymph node sections can be incubated with and without the agent, and the number of bound lymphocytes and/or malignant cells determined. The antagonists can be preincubated with lymph node sections (a non-competitive assay) or simultaneously added with lymphocytes to the lymph node sections (a competitive assay).

Such a screen can also be used to customize an anti-metastasis treatment to an individual patient, and allows the practitioner to identify and select those agents or combinations thereof that have the best ability to inhibit CLEVER-1 malignant cell binding to vascular and/or lymphatic endothelium in such patient, and thus maximize the benefit of the treatment with such agents for such patient.

Additionally, such in vitro assay allows the practitioner to select for agents that provide a beneficial effect on disrupting malignant cell: CLEVER-1 containing endothelium interactions, nevertheless, minimize, if possible, the effect of such treatment on CLEVER-1 mediated leukocyte binding, An antagonist can inhibit malignant cell or lymphocyte cell migration into or out of the lymph nodes. In a preferred embodiment, antagonists would inhibit both entrance and exit of an undesired cell into and out of the lymph nodes, respectively. As such, malignant tumor cells would preferably be prevented from entering a lymph node, and establishing there, and any that did enter the lymph nodes via an afferent lymph vessel independent mechanisms would be contained, thus slowing metastasis.

This assay can be used further to monitor the efficacy of chemotherapy treatments administered to an individual, said individual being a human or an animal, in need thereof. Samples can be analyzed before, during, and after chemotherapy for the presence of malignant tumor cells that bind to CLEVER-1 or antigenic fragments thereof, or CLEVER-1 binding compounds.

In a further embodiment, purified CLEVER-1 protein, or fragments thereof can be used for high volume screening of antagonists that are capable of preventing or lowering the ability of a leukocyte or malignant cell to adhere to endothelial cell CLEVER-1. CLEVER-1 protein, or fragments thereof can be attached to a solid support matrix, including but not limited to a microtiter plate, an agarose column, or magnetic beads, using standard methods well known in the art. Antagonists can be screened for interaction with CLEVER-1 or fragments thereof, either in the absence or presence of leukocytes. Leukocytes or malignant cells can be labeled with fluorescent dyes such as, for example, bis-carboxyethyl carboxyfluorescein or fluorescein isothiocyanate and the number of bound cells in presence or absence of the antagonists can be analyzed by a fluoroimager.

The high volume screen assay of this aspect of the invention can be used to screen combinatorial libraries for molecules that inhibit the binding of leukocytes and malignant tumor cells to CLEVER-1 or a fragments thereof. Antagonists that show strong affinity for purified CLEVER-1 protein or fragments thereof can be screened further using the in vitro adhesion assay described above.

Antibodies used in the methods of the invention as CLEVER-1 binding compounds are preferably antibodies with a specificity against CLEVER-1, or an antigenic fragment thereof. Such antibodies can be polyclonal or monoclonal.

Another potential CLEVER-1 antagonist is a peptide derivative of the CLEVER-1 polypeptide that are naturally or synthetically modified analogs of the polypeptides that have lost biological function yet still recognize and bind to the ligand of the polypeptides to thereby effectively block the interaction of said ligand with CLEVER-1. Examples of peptide derivatives include, but are not limited to, small peptides or peptide-like molecules.

Another potential human CLEVER-1 antagonist is a peptide derivative of the ligand polypeptides which are naturally or synthetically modified analogs of the polypeptides that have lost biological function yet still recognize and bind to CLEVER-1 to thereby effectively block CLEVER-1. Examples of peptide derivatives include, but are not limited to, small peptides or peptide-like molecules.

The present invention relates to a diagnostic method for the detection of cells that contain CLEVER-1, that is, CLEVER-1 positive cells, in samples taken from the human or animal body. Such a method would involve the use of CLEVER-1 binding compounds, including but not limited to, monoclonal and polyclonal antibodies, with specificity for CLEVER-1. Such compounds can be labeled with a substance, such as a colorimetric dye or radioactive molecule, to permit rapid and easy detection of binding of the compound to cells that express CLEVER-1.

Therapeutic Uses of CLEVER-1 Antagonists

In another embodiment, the present invention relates to a method of treating malignant carcinomas. It is common for carcinomas to metastasize first to the regional lymph nodes (Sleeman, J. P., *Recent Results Cancer Res.* 157:55-81 (2000)). As described herein, CLEVER-1 is involved in the entrance and exit of malignant tumor cells to and from the lymph nodes. As such, antagonists that inhibit malignant tumor cell binding to CLEVER-1, including but not limited to, monoclonal and polyclonal antibodies, peptides, small molecule inhibitors, drugs, and other such agents can reduce metastasis and serve as effective chemotherapeutic agents.

In another aspect, the present invention relates to a method of treating disorders where the leukocyte-endothelial cell adhesion reaction is associated with acute or chronic inflammatory diseases such as skin inflammations, diabetes, connective tissue diseases (such as lupus, rheumatoid arthritis, ostheoarthritis), obstructive and restrictive lung diseases (such as asthma, ARDS, sarcoidosis, idiopathic pulmonary fibrosis), inflammatory bowel diseases (such as ulcerative colitis and Crohn's disease), various nephritides, non-viral hepatitis, cirrhosis, cholangitis, atherosclerosis, vasculitis, thyroiditis, multiple sclerosis, myositis, ischemia reperfusion injury, transplantation rejection.

The antagonists can also be employed to treat histamine-mediated allergic reactions and immunological disorders including late phase allergic reactions, chronic urticaria, and atopic dermatitis. IgE-mediated allergic reactions such as allergic asthma, rhinitis, and eczema can also be treated.

The antagonists can also be employed to treat chronic and acute inflammation by preventing the extravasation of leukocytes to a wound area. They can also be employed to regulate normal pulmonary macrophage populations, since chronic and acute inflammatory pulmonary diseases are associated with sequestration of mononuclear phagocytes in the lung.

Antagonists can also be employed to treat rheumatoid arthritis by preventing the extravasation of leukocytes into synovial fluid in the joints of patients. Monocyte influx and activation plays a significant role in the pathogenesis of both degenerative and inflammatory arthropathies.

The antagonists can also be employed to treat asthma and allergy by preventing eosinophil accumulation in the lung. The antagonists can also be employed to treat subepithelial basement membrane fibrosis which is a prominent feature of the asthmatic lung.

The antagonists can also be employed for treating atherosclerosis, by preventing monocyte infiltration in the artery wall.

The antagonists can be employed in a composition with a pharmaceutically acceptable carrier, e.g., as hereinafter described.

Formulations of Compounds

The antagonists of CLEVER-1 can be used as therapeutic compositions. The antagonists of CLEVER-1 can be administered as a single dose or in multiple doses. The antagonists of the present invention can be administered either as an independent therapeutic regime or in combination with other therapeutic agents. The antagonists can be combined with conventional therapies, which can be administered simultaneously or sequentially.

Such therapeutic compositions can consist solely of the antagonist of CLEVER-1 although, preferably, the compositions will contain the antagonist of CLEVER-1 combined in admixture with a pharmaceutically acceptable carrier vehicle. Suitable vehicles and their formulation, inclusive of other human proteins, e.g., human serum albumin, are described for example in Remington: The Science and Practice of Pharmacy, Gennaro, Alfonso, 20th ed. (2000). In order to form a pharmaceutically acceptable composition that is suitable for effective administration to a patient in need of such composition, such compositions will contain an effective amount of the antagonist of CLEVER-1 together with a suitable amount of carrier vehicle.

Compositions containing antagonists of CLEVER-1 can be administered perorally, intravenously, intramuscularly, or sub-cutaneously at the appropriate dosages, which will depend upon the severity of the condition of the patient and upon such criteria as the patient's height, weight, sex, age, and medical history. The dose will also depend upon whether the compound of the invention is being administered to a human patient or in a veterinary setting to an animal, in need thereof.

For the purpose of parenteral administration, compositions containing the antagonists of CLEVER-1 are preferably dissolved in distilled water and the pH-value is preferably adjusted to about 6 to 8. In order to facilitate the lyophilization process resulting in a suitable product, lactose can be added to the solution. Preferably, the solution is then filtered sterilized, introduced into vials, and lyophilized. In a preferred embodiment, the compound of the invention is administered orally to a patient, at the time of eating or shortly thereafter. The concentration of the antagonists of CLEVER-1 in these composition, whether oral or parenteral, can vary, e.g., from $10^{-12}$ M to $10^{-3}$ M.

Additional pharmaceutical methods can be employed to control the duration of action. Controlled release preparations can be achieved by the use of polymers to complex or adsorb the antagonists of CLEVER-1. The controlled delivery can be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the antagonists of CLEVER-1 into particles of a polymeric material such as polyesters, polyamino acids, hydrogels, poly (lactic acid) or ethylene vinylacetate copolymers. Alternatively, instead of incorporating the CLEVER-1 antagonists into these polymeric particles, it is possible to entrap these derivatives in microcapsules prepared, for example, by coacervation techniques or by interfacial polymerization, for example, bydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in Remington: The Science and Practice of Pharmacy, Gennaro, Alfonso, 20th ed. (2000).

The following Example serves only to illustrate the invention, and is not to be construed as in any way limiting the invention.

EXAMPLE 1

Production of Monoclonal Antibodies

Balb/c mice were immunized to footpads four times at one week intervals, with incomplete Freund's adjuvant containing suspension made from lymphatic vessels excised from human lymph nodes under stereo microscope. The suspension was made by cutting the vessels to small pieces by scissors and the pieces in phosphate buffered saline were then drawn back and forth into a syringe connected to a 21 q needle. The popliteal lymph node lymphocytes from the immunized mice were isolated by a glass homogenizer. The popliteal lymph node lymphocytes of the immunized mice were fused with Sp2/0 myeloma cells. Hybridoma supernatants were primarily tested on frozen sections of human lymph nodes using immunoperoxidase staining. The testing conditions were the same for antibodies 3-266 and 3-372 generated by two of the hybridomas.

Immunoperoxidase stainings were performed as described (Salmi, *Science* 257:1407-1409 (1992)). Briefly, acetone fixed 6 μm frozen sections from different human tissues (lymph nodes, appendix, bronchus, cerebellum, epididymis, esophagus, heart, small and large intestine, kidney, liver, lung, normal and psoriatic skin, synovium, testis and tonsil) were stained with antibody 3-266, 3-372 or 3G6, a negative class matched control antibody for 3-266 and 3-372 (mouse IgG1) and 3,3-diaminobenzidine was used as a substrate. Procedures for tissue collection were approved by the Local and National Boards of Medicolegal Affairs in Finland.

Two of the hybridomas produced antibodies (3-266 (DSM ACC2519) and 3-372 (DSM ACC2590)) that clearly stained lymphatic endothelium both in afferent and efferent lymphatic systems and vascular endothelium on HEV, while the other structures remained unstained. The staining of the lymphatic endothelium is shown in FIG. 1. FIG. 1 is an indirect immunoperoxidase staining that shows that monoclonal antibodies 3-266 and 3-372 recognize endothelium both in afferent and efferent lymphatic systems and on HEV. FIGS. 1*a*-1*c* are from the skin. FIGS. 1*d*-1*i* are from a lymph node. FIGS. 1*a*, 1*d* and 1*g* show the staining with monoclonal antibody 3-266, FIGS. 1*b*, 1*e* and 1*h* show the staining with monoclonal antibody 3-372 and FIGS. 1*c*, 1*f* and 1*i* show the staining with a negative control antibody, 3G6. In FIGS. 1*a*, 1*b* and 1*c*, the arrows point to the epithelium and arrowheads to afferent lymphatics. In FIGS. 1*d* and 1*e*, the arrows point to the lymphatic vessels (lymphatic sinusoids that belong to the efferent lymphatic system) within the lymph node. In FIGS. 1*g* and 1*h*, the arrows point to HEV.

EXAMPLE 2

Determination of Molecular Weight of CLEVER-1

Molecular weight determination was performed by immunoblotting. One percent NP-40 lysates containing of human lymph nodes was analyzed using 5-12.5% sodium dodecyl sulphate-polyacrylamide gel electrophoresis (SDS-PAGE). SDS-PAGE was run in non-reducing conditions. The molecules in the gel were blotted overnight to nitrocellulose sheets and probed with 3-266, 3-372 or a negative control antibody (3G6) (Salmi, M. et al., *J. Exp. Med.* 183:569-579 (1996). Peroxidase conjugated rabbit anti-mouse Ig was used as the second stage reagent. Detection was performed using enhanced chemiluminescence system according to the instructions of the manufacturer (Amersham).

Figure 2:
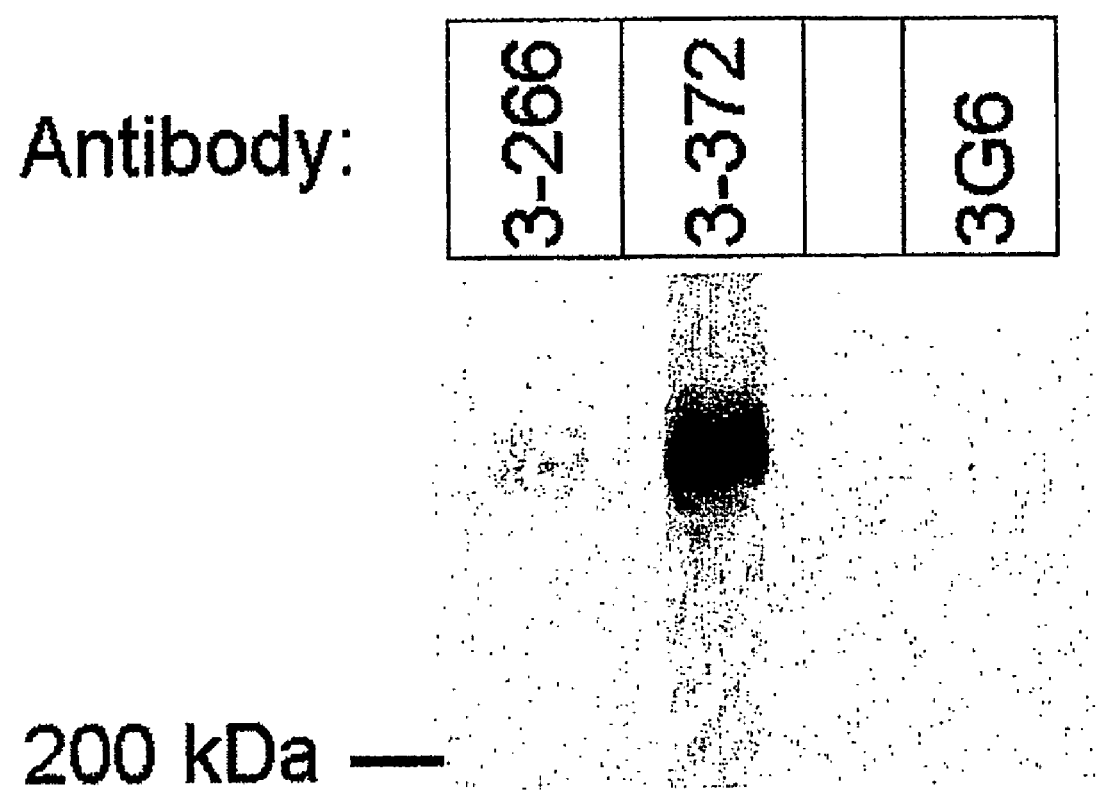

Both antibodies recognized a molecule of the same size (about 270-300 kDa; FIG. 2). Due to this and an identical staining pattern, these antibodies were assumed to recognize the same antigen and this antigen was named CLEVER-1.

EXAMPLE 3

Purification and Molecular Characterization of CLEVER-1

The molecule recognized by 3-372 antibody was purified from human lymph node lysate overnight (lysis buffer: 150 mM NaCl, 10 mM Trisbase, pH 7.2, 1.5 mM MgCl2, 1% NP-40, 1% aprotinin, and 1 mM PMSF) as described in Smith, D. J. et al., *J. Exp. Med.* 188:17-27 (1998). After centrifugation, the lysate supernatant was applied sequentially to immunoaffinity columns containing CnBr-activated Sepharose beads armed with irrelevant mAbs and 3-372 (3 mg/ml beads). After washing with lysis buffer, the antigens recognized by 3-372 were eluted with 50 mM triethylamine, frozen and subsequently lyophilized. The eluted material was then subjected to SDS-PAGE analysis and silver staining (O'Connell, K. L. and Stults, J. T., *Electrophoresis* 18:349-359 (1997)). The specific band was excised, reduced, alkylated and digested with trypsin (Promega) overnight at +37° C. as described (Shevchenko, A. et al., *Anal. Chem.* 68:850-855 (1996); O'Connell, K. L. and Stults, J. T., *Electrophoresis* 18:349-359 (1997)). The peptides were analyzed using PerSeptive BioSystems Voyager DE-PRO mass spectrometer operated in the reflectron delayed-extraction mode. Calibration of the spectrum was performed internally by using autolysis products of trypsin or with added calibration mixture 2 (PerSeptive BioSystems). Database search was performed by MS-Fit algorithm (prospector.ucsf.edu/ucsfhtml3.2/msfit.htm) of the University of California, San Francisco mass spectrometry facility.

After cleavage with trypsin, mass spectrometric analyses yielded 27 peptides. 21 (77%) of those had identical nucleotide sequences with two Genebank entries: AJ 275213, a submission for a cDNA clone called stabilin-1, and D87433, a cDNA clone KIAA0246 isolated from the cell line KG-1. The peptide sequences covered altogether 268 amino acids (100% of the 2570 amino acids of stabilin-1) and spanned the amino acids between 53 an 2301.

Next we designed primers based on the peptide sequences, the 5' end of the cDNA for stabilin-1 and the 3' end of the cDNA of KIAA0246 and used them to make several RT-PCR fragments that were then ligated together to clone the full-length 7879 bp cDNA (SEQ ID NO:1). Sequencing of the whole construct revealed a high homology with the existing 3' end KIAA0246 sequence available in the data bank. However, it contained 4 nucleotide differences, when compared to the Stabilin sequence. They all cause a change at the amino acid level. Two of these changes are identical with the genomic sequence data available from the HUGO project (AC 006208), but since the genomic clone only covers about half of the gene for this cDNA, the nature of the two other changes remains to be determined.

Figure 7:
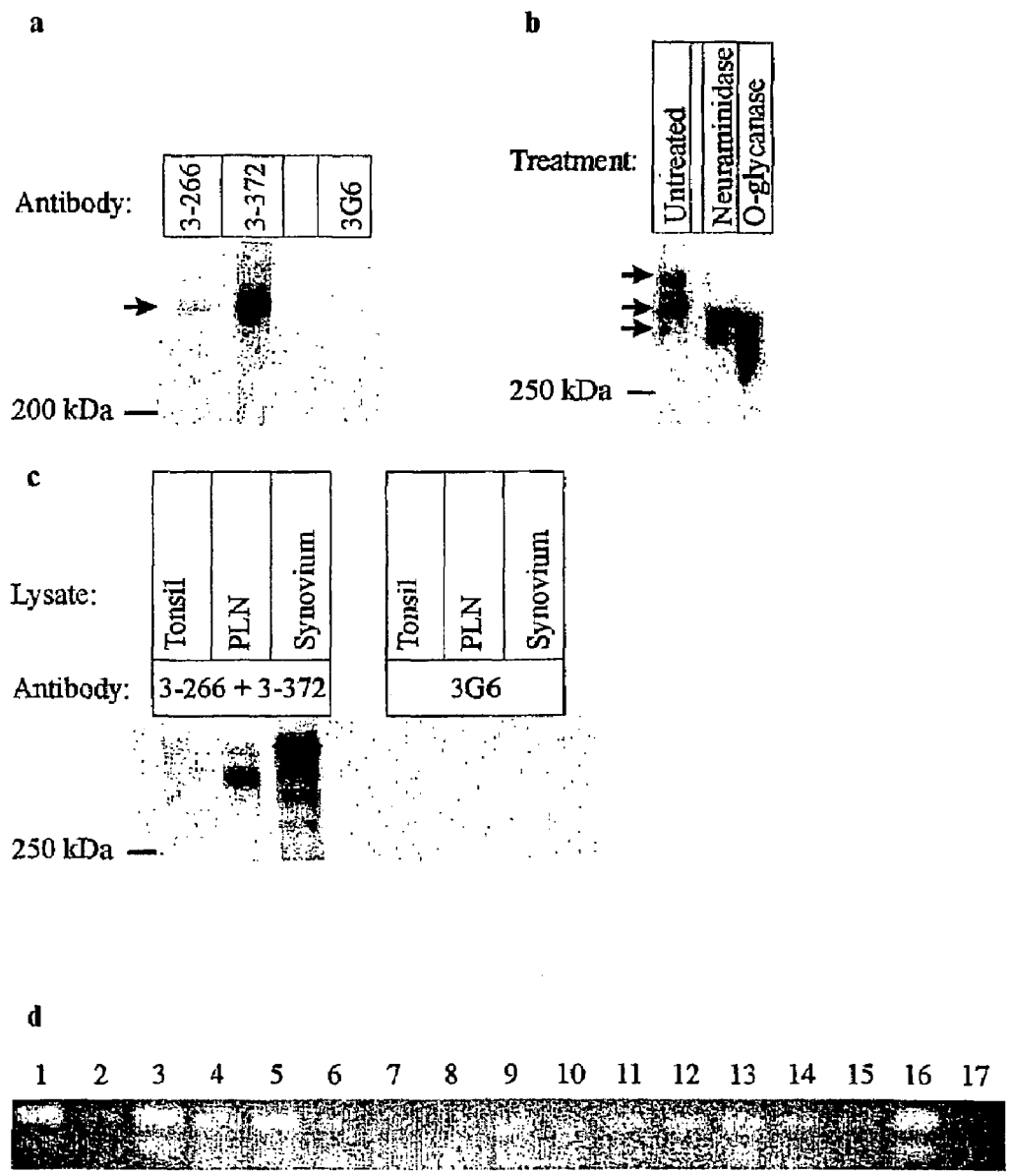
FIG. 7. Molecular characterization of CLEVER-1. (a) Antibodies 3-266 and 3-372 recognize a 270-300 kDa molecule in immunoblotting. 3G6 is a negative control antibody. (b) In gels run 48 hr for better resolution, at least three different isoforms of CLEVER-1 are seen, and enzymatic digestions with neuraminadase and O-glycans reveal the sialoglycoprotein nature of CLEVER-1. (c) Relative contribution of different isoforms of CLEVER-1 is different in tonsil, lymph nodes and synovium. (d) An alternative spliced form missing exon 27 is present in 1. lung, 2. brain, 3. placenta, 4. heart, 5. liver, 6. skeletal muscle, 7. kidney, 8. pancreas, 9. spleen, 10. thymus, 11. prostata, 512. testis, 13. ovary, 14. small testine, 15 colon, 16. lymph nodes. Water control negaive (lane 17). The upper band represents the standard form and the lower one is the splice variant of CLEVER-1.

Sequencing of several different CLEVER-1 cDNA-clones also revealed the existence of at least two alternatively spliced isoforms of the molecule: the regions covered by exons 23 (nucleotides 2377-2562) and 27 (nucleotides 2914-3009) can be spliced out. We could confirm the existence of one of those splice variants (lacking exon 27) also at the mRNA level (FIG. 7) but the second one (lacking exon 23) that we cloned from a human peripheral lymph node library was not visible in the system suggesting a low abundance/turnover of the mRNA encoding this form.

The sequence comparisons revealed significant homologies to proteoglycan link protein-like sequence, epidermal growth factor-like repeats and two RGD motifs being well in line with the adhesive properties of CLEVER-1.

EXAMPLE 4

In Vitro Adhesion Assay

Lymph node sections were first incubated with 3-266, 3-372 or control antibodies against human HLA ABC (HB-95, ATCC and 3G6 (against chicken T cells) and then overlaid with Ficoll gradient (Pharmacia) purified peripheral blood mononuclear cells or different human tumor cell lines (lymphoblastoid cell lines, KCA and IBW4; a Burkitt lymphoma CRL-1648; squamocellular carcinoma lines NA and NU). Thereafter, the sections were subjected to two different types of assays: 1. A non-static assay, which optimally measures binding of cells to HEV and is performed under rotatory conditions (60 rpm on orbital shaker for 30 min at +7° C.). 2. A static assay, in which the sections overlaid with cells are let to stay in static conditions for 15 min, followed by 5 min of rotation at 60 rpm and then again 15 min without rotation at 7° C. (Static conditions were needed to optimal binding to lymphatic endothelium). The adherent cells were fixed in 1% glutaraldehyde. The number of lymphocytes bound to HEV and to sinusoidal (lymphatic) endothelium was counted single blind under dark-field illumination in which setting the sinusoidal vessels are easily recognizable. The results of the inhibition assays are presented as percentage of control binding (the number of adherent cells/vessel in the presence of control mAb defines 100% adherence).

When the assay was performed in non-static conditions, mimicking the blood flow, lymphocyte binding to HEV was reduced 43.6% and 45.2% by 3-266 and 3-372, respectively (FIG. 3A). To mimic the conditions at sites of lymphocyte exit, the assay was performed in static conditions. In these assays lymphocyte binding to lymphatic endothelium was decreased 46.4% and 64% by 3-266 and 3-372, respectively (FIG. 3B). These data indicate that the molecule recognized by 3-266 and 3-372 indeed mediate lymphocyte binding both to HEV and to lymphatic endothelium.

Figure 3:
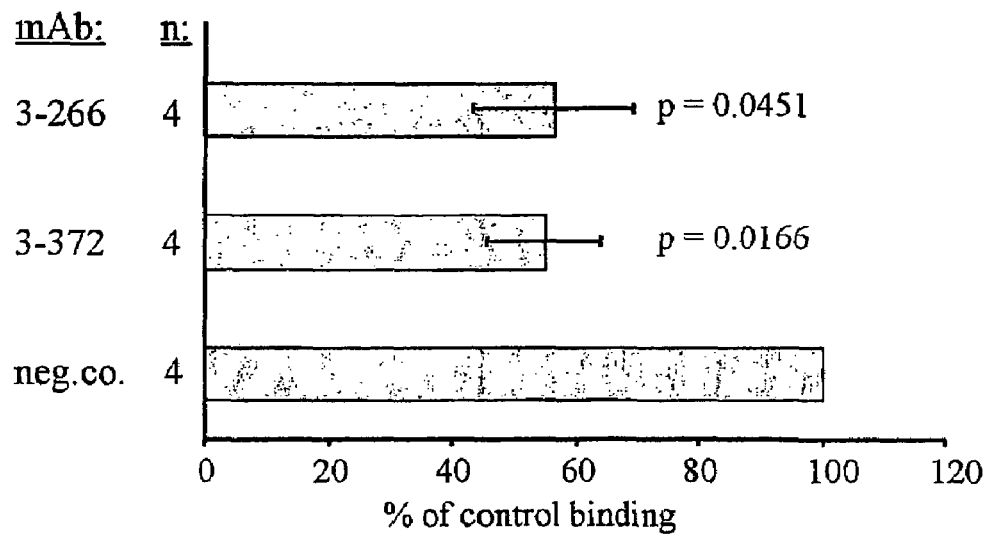
FIGS. 3A and 3B. CLEVER-1 is involved in lymphocyte binding to endothelial ells both in HEV and lymphatics. An adhesion assay was performed to measure lymphocyte binding to HEV (FIG. 3A) and to lymphatic endothelium (FIG. 3B). The sections were pre-incubated with monoclonal antibody 3-266 or 3-372, or negative control antibody anti-HLA ABC or 3G6 ("neg co") after which the sections were overlaid with normal lymphocytes. The results of three to four independent inhibition experiments are shown as mean percentage of maximal binding±SEM.
Figure 3:
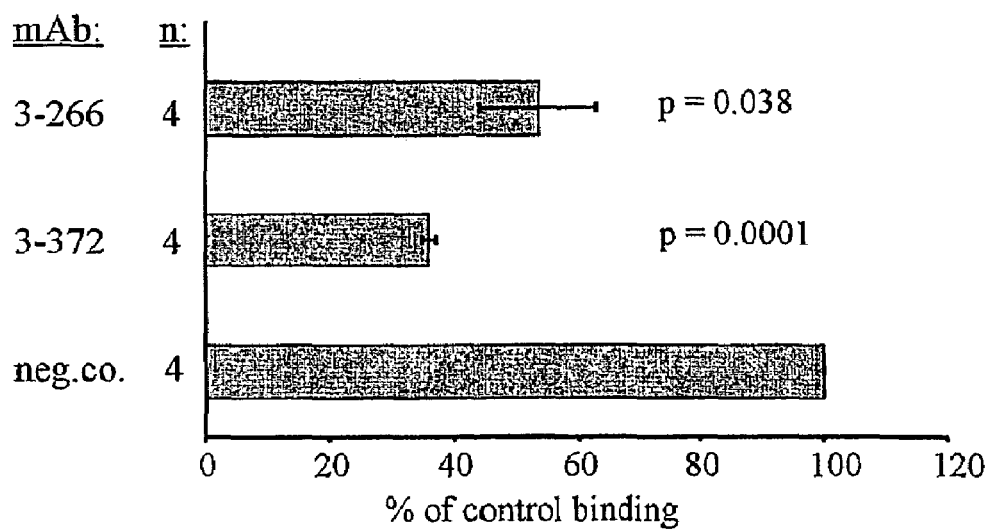
Figure 4:
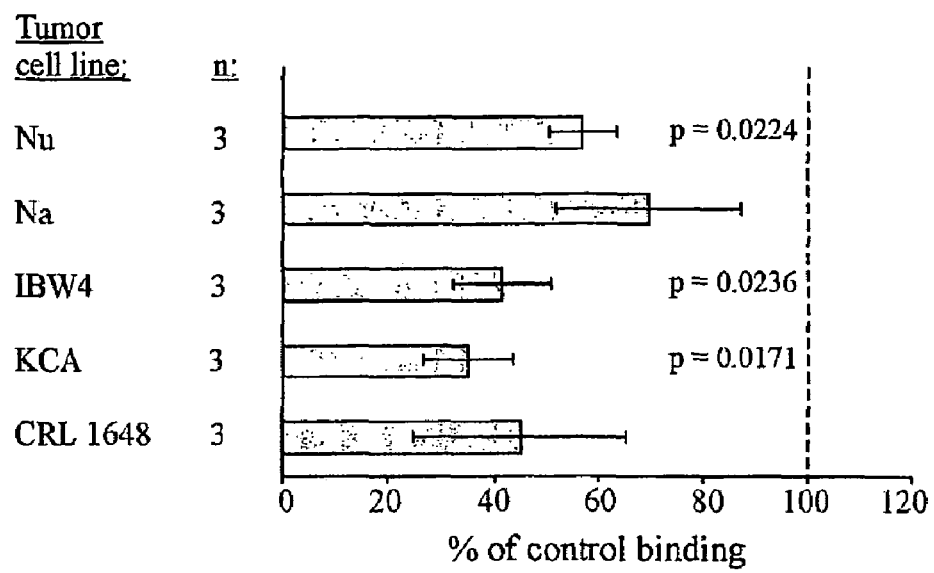
FIGS. 4A and 4B. CLEVER-1 is involved in binding of tumor cells to endothelial cells both in HEV and lymphatics. An adhesion assay was performed to measure binding of different tumor cell lines to HEV (FIG. 4A) and to lymphatic endothelium (FIG. 4B). The sections were pre-incubated with 3-372 or negative control antibody (anti-HLA ABC) after which the sections were overlaid with different tumor cells: Nu, NA, IBW4, KCA and CRL 1648. The results of three to four independent inhibition experiments are shown as mean percentage of maximal binding±SEM.
Figure 4:
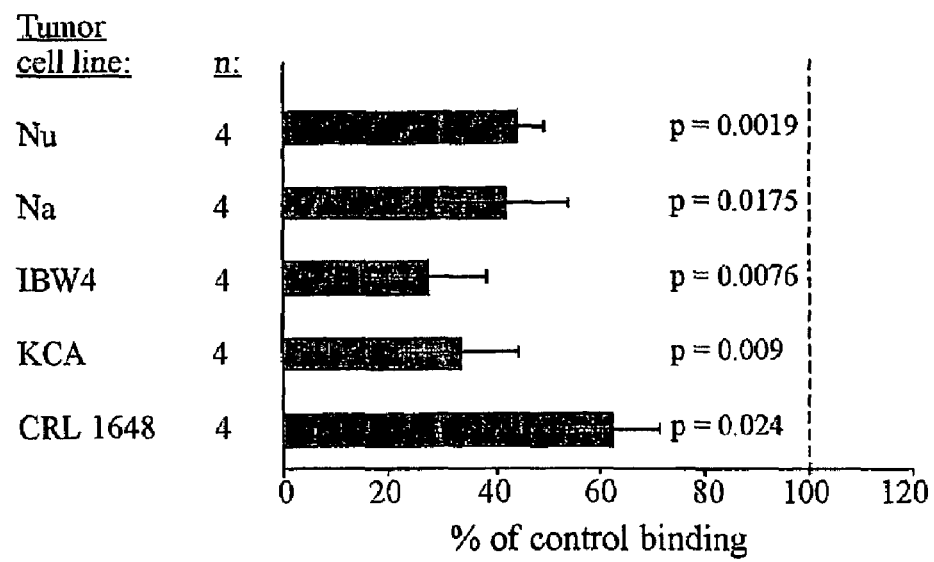

To study the role of this molecule in migration of malignant cells, the assays were performed using three lymphoma cell lines (CRL 1648, KCA and IBW4) and two squamocellular carcinoma cell lines (NA and NU). For these assays 3-372 antibody was chosen because of its higher inhibitory capacity (FIG. 3). The results of these experiments clearly demonstrated that CLEVER-1 is also involved in binding of malignant cells to endothelium both at entrance and exit sites within the lymph nodes (FIGS. 4A and 3).

EXAMPLE 5

CLEVER-1 is Upregulated at Sites of Inflammation on HEV-like Vessels

Figure 5:
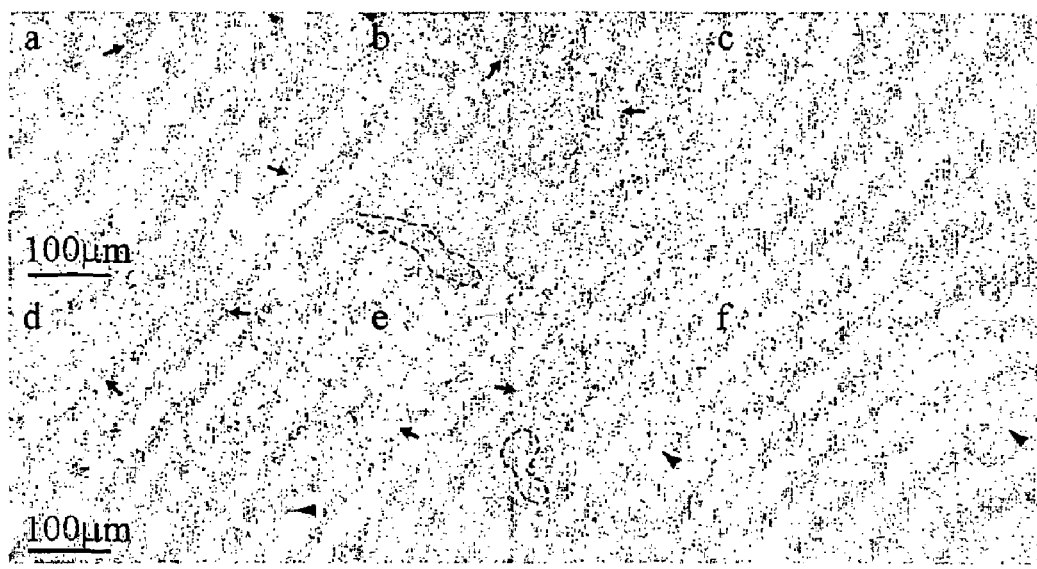
FIG. 5. CLEVER-1 is induced on HEV-like vessels at sites of inflammation in connection to infiltrations of inflammatory cells (FIGS. 5a-5c, synovium.

Synovial samples from 18 patients suffering from chronic arthritis and undergoing synovectomies, skin samples from diseased skin of patients suffering from psoriasis (n=5), lichen (n=1), mycosis fungoides (n=1), erythrodermia (n=2), exanthema (n=1), folliculitis (n=3) and normal skin samples from 15 individuals were studied for expression of CLEVER-1 using immunoperoxidase method as described above. Like in normal non-lymphoid tissues CLEVER-1 was present in afferent lymphatic vessels in inflamed synovial and both in normal and diseased skin samples. In addition, CLEVER-1 expression was induced on HEV-like vessels that appear at sites of inflammation and are surrounded by heavy infiltrations of inflammatory cells (FIG. 5). Table 2 illustrates complete correlation between the extent of inflammatory infiltration and upregulation of CLEVER-1 expression in synovial samples. The same phenomenon was observed in skin samples: all diseased skin samples had inflammatory infiltrations that contained CLEVER-1 positive HEV-like vessels. Those vessels were absent in normal skin samples.

EXAMPLE 6

Figure 6:
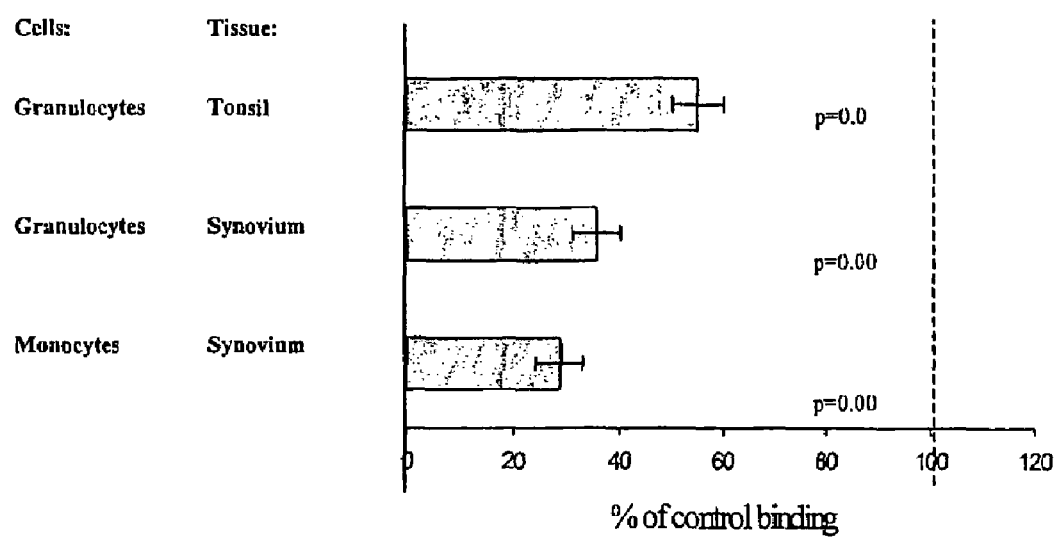
FIG. 6. CLEVER-1 mediates binding of monocytes and granulocytes to HEV-like vessels at sites of inflammation. Contribution of CLEVER-1 in binding of monocytes and granulocytes to inflamed synovial vessels and binding of granulocytes to tonsil was tested using Stamper-Woodruff type of binding assay. 3-372 and 3-266 (pooled) but not the class-matched control antibody (3G6) significantly inhibited binding of granulocytes and monocytes to HEV-like vessels in the organs tested. The results of four independent assays are shown as mean percentage of maximal binding (=100% in the presence of the control antibody)±SEM.

Clever-1 Also Mediates Binding of Monocytes and Granulocytes to HEV-like Vessels Human monocytes from peripheral blood were purified from Ficoll-gradient (Pharmacia) isolated mononuclear cells by letting them to adhere to plastic surfaces for an hour at +37° C. Granulocytes were purified from leukocyte rich buffy coats from human blood using Percoll-gradient (Pharmacia) centrifugation. Their binding was tested to HEV-like vessels in inflamed synovium. In addition, granulocyte binding was tested to tonsil HEV that brightly express CLEVER-1. (When tonsils are removed they always have variable extent of inflammation, although they as a lymphoid organ have HEV without any inflammation). Both granulocytes and monocytes bound efficiently to HEV-like vessels in inflamed synovium and granulocytes adhered avidly to HEV in tonsils. Their binding to these organs was significantly inhibited by the antibody pool containing 3-372 and 3-266 but not with the control antibody (FIG. 6).

EXAMPLE 7

CLEVER-1 Controls Lymphocyte Trafficking in Vivo

Figure 8:
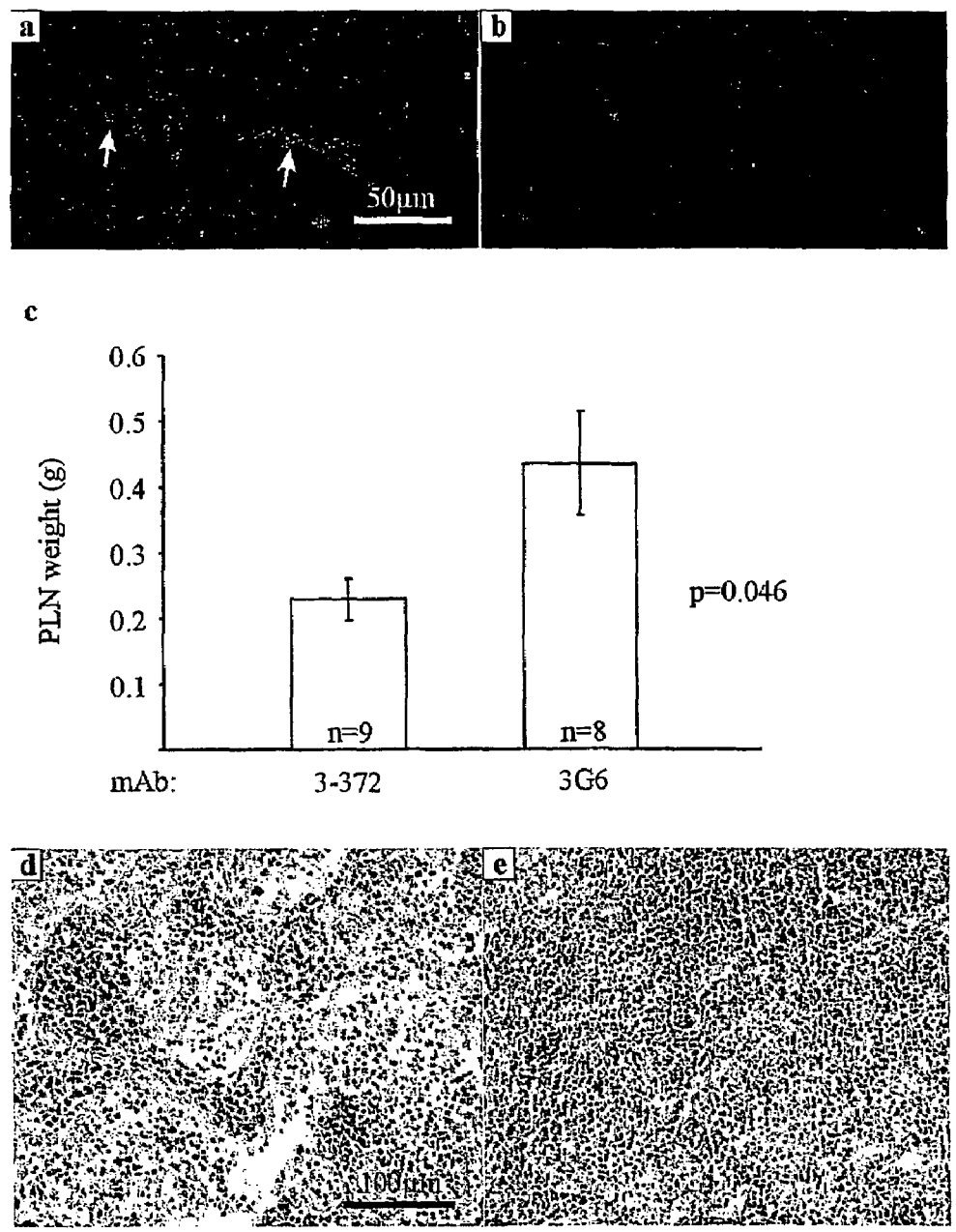
FIG. 8. CLEVER-1 is expressed on the surface of endothelium in vivo and inhibition of its function blocks lymphocyte trafficking. Intravenously given 3-372 antibody (a) but not a negative class-matched control antibody (b) localized on the surface of HEV in lymph nodes after a 5 min circulation. HEV is pointed out by arrows in a. (c) Anti-CLEVER antibody treatment significantly inhibits the increase of the size of the lymph nodes draining the footpads. (One lymph node of a 3-372 treated rabbit was not found). (d) Lymphatic sinusoids of 3-372 treated animals contained less lymphocytes than those of control treated rabbits (e).

In order to verify that CLEVER-1 has a functional role in vivo, it was at first confirmed by intravenous injection of 3-372 antibody that rabbits express CLEVER-1 on the surface of endothelium in vivo. The presence of CLEVER-1 on HEV was detected after the 3-372 antibody had circulated 5 minutes in vivo using frozen sections and FITC labelled anti-mouse IgG second stage antibody after sacrification (FIG. 8a). In this time frame the intravenously given 180 kDa immunoglobulin molecule does not have a possibility to leak and diffuse into the tissue. Based on these results antibody 3-372 (and a class-matched negative control antibody) was given to the rabbits immunized with keyhole limpet hemocyanin to footpads and the effects of the antibody treatment on the size and cellularity of the lymph nodes draining the footpads was analyzed.

Antibody treatment against CLEVER-1 significantly prevented increase of the size of the popliteal lymph nodes (FIG. 8c) indicating that CLEVER-1 has a functional role in lymphocyte traffic in vivo. Most likely it exerts its effects both at lymphocyte entrance in HEV and their exit in lymphatic sinusoids, because the rabbits treated with 3-372 antibody had only few lymphocytes in their lymphatic sinusoids when analyzed using histological section (FIG.

8d) Intravenously given 3-372 antibody was also detected to bind CLEVER-1 on lymphatic sinuses when tested at sacrification 3 days after the final 3-372 dose. No signal was detected in rabbits which received a control antibody (data not shown).

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

TABLE 1

Matches with CLEVER-1 and stabilin-1
1. 21/27 matches (77%). 275350.0 Da, pI = 6.04. Acc. #6469374. *HOMO SAPIENS*. (AJ275213) stabilin-1.

| m/z submitted | MH+ matched | Delta ppm | start | end | Peptide Sequence (Click for Fragment Ions) | Modifications |
|---|---|---|---|---|---|---|
| 775.488 | 775.483 | 6.4034 | 372 | 377 | (R)VFLQLR(V) (SEQ ID NO:2) | |
| 787.36 | 787.3739 | -17.6253 | 1299 | 1305 | (R)SGFSFSR(G) (SEQ ID NO:3) | |
| 799.495 | 799.5042 | -11.4617 | 1585 | 1591 | (R)VGLELLR(D) (SEQ ID NO:4) | |
| 812.495 | 812.4994 | -5.4309 | 1047 | 1053 | (R)TLPNLVR(A) (SEQ ID NO:5) | |
| 917.502 | 917.4997 | 2.4556 | 1040 | 1046 | (R)AFWLQPR(T) (SEQ ID NO:6) | |
| 1017.44 | 1017.425 | 14.4862 | 2295 | 2301 | (R)WDAYCFR(V) (SEQ ID NO:7) | |
| 1104.54 | 1104.526 | 12.6406 | 53 | 61 | (K)QTCPSGWLR(E) (SEQ ID NO:8) | |
| 1212.7 | 1212.695 | 3.9482 | 1021 | 1032 | (R)VTALVPSEAAVR(Q) (SEQ ID NO:9) | |
| 1284.65 | 1284.622 | 21.4530 | 1678 | 1688 | (R)EGSIYLNDFAR(V) (SEQ ID NO:10) | |
| 1291.79 | 1291.774 | 12.5434 | 613 | 624 | (R)ILLGPEGVPLQR(V) (SEQ ID NO:11) | |
| 1330.63 | 1330.575 | 41.7401 | 953 | 965 | (R)AGNGGCHGLATCR(A) (SEQ ID NO:12) | |
| 1330.63 | 1330.633 | -1.9754 | 1873 | 1812 | (R)CDHFBTRPLR(L) (SEQ ID NO:13) | |
| 1374.66 | 1374.632 | 20.1117 | 62 | 72 | (R)ELPDQITQDCR(Y) (SEQ ID NO:14) | |
| 1456.79 | 1456.776 | 9.6229 | 1069 | 1082 | (R)LGGQEVATLNPTTR(W) (SEQ ID NO:15) | |
| 1493.8 | 1493.796 | 2.4215 | 508 | 521 | (R)TIGQILASTEAPSR(F) (SEQ ID NO:16) | |
| 1555.7 | 1555.663 | 23.5678 | 219 | 231 | (R)CLPGYTQQGSECR(A) (SEQ ID NO:17) | |
| 1678.94 | 1678.913 | 16.1953 | 1802 | 1817 | (R)NVEALASDLPNLGPLR(T) (SEQ ID NO:18) | |
| 1730.89 | 1730.887 | 1.9674 | 1054 | 1068 | (R)AHPLQGALFEEELAR(L) (SEQ ID NO:19) | |

TABLE 1-continued

Matches with CLEVER-1 and stabilin-1
1. 21/27 matches (77%). 275350.0 Da, pI = 6.04. Acc. #6469374. *HOMO SAPIENS*. (AJ275213) stabilin-1.

| m/z submitted | MH⁺ matched | Delta ppm | start | end | Peptide Sequence (Click for Fragment Ions) | Modifications |
|---|---|---|---|---|---|---|
| 1912.82 | 1912.832 | -6.3742 | 936 | 952 | (K)LGEAGDGYQCSPIDPCR(A) (SEQ ID NO:20) | |
| 2057.05 | 2057.03 | 9.5484 | 1655 | 1673 | (R)SEDLLEQGYATALSGHPLR(F) (SEQ ID NO:21) | |
| 2165.11 | 2165.14 | -13.6320 | 1707 | 1725 | (R)VLLPPEALHWEPDDAPIPR(R) (SEQ ID NO:22) | |
| 2295.22 | 2295.224 | -1.5853 | 389 | 410 | (R)EILTTAGPFTVLVPSVSSFSSR(T) (SEQ ID NO:23) | |

6 unmatched masses: 871.5410 949.4800 1360.6500 1538.6900 1787.9200 2008.1400
The matched peptides cover 10% (268/2570 AA's) of the protein.
Coverage Map for This Hit (MS-Digest index #): 427477

TABLE 2

CLEVER-1 Expression Is Induced Mainly on Vessels Surrounded by Lymphocytic Infiltrations in Inflamed Synovia

| Expression of CLEVER-1 on HEV-like vessels[1] | The degree of inflammatory infiltration[2] | |
|---|---|---|
| | 0/1 (n = 9) | 2/3 (n = 9) |
| -/± | 100% | 0 |
| ++/+++ | 0 | 100% |

[1]Intensity was scored as −, ±, + negative or weak, ++, +++ moderate or strong.
[2]Degree of the inflammatory cell infiltration in 18 synovial samples was scored as: 0/1, none or few lymphocytes around the vessels, 2/3 marked or massive lymphocytic infiltrations.

What is claimed is:

1. A method of treating inflammation in a patient in need of the same, said method comprising administering, to said patient, an agent that inhibits CLEVER-1 mediated leukocyte binding, wherein said agent is a CLEVER-1 antagonist antibody or a fragment thereof that contains an antigen binding site and wherein said CLEVER-1 antagonist antibody is antibody 3-266 produced by the hybridoma DSM ACC2519 or antibody 3-372 produced by the hybridoma DSM ACC2590, or said fragment thereof, or chimeric, humanized or primitized antibody thereof.

2. A method of treating inflammation in a patient in need of the same, said method comprising administering an agent that inhibits CLEVER-1 mediated leukocyte binding to said patient, wherein said inhibiting agent is antibody 3-266 produced by the hybridoma DSM ACC2519, or fragment thereof that contains an antigen binding site.

3. A method of treating inflammation in a patient in need of the same, said method comprising administering an agent that inhibits CLEVER-1 mediated leukocyte binding to said patient, wherein said inhibiting agent is antibody 3-372 produced by the hybridoma DSM ACC2590, or fragment thereof that contains an antigen binding site.

4. The method of claim 1, wherein said antibody is a monoclonal antibody.

5. Antibody is said chimeric, humanized or primatized antibody.

6. The method of claim 1, wherein said antibody is said antibody fragment.

7. The method of claim 6, wherein said fragment is a Fab, F(ab')$_2$ or Fv antibody fragment.

* * * * *

UNITED STATES PATENT AND TRADEMARK OFFICE
CERTIFICATE OF CORRECTION

| | |
|---|---|
| PATENT NO. | : 7,354,577 B2 |
| APPLICATION NO. | : 10/497991 |
| DATED | : April 8, 2008 |
| INVENTOR(S) | : Jalkanen et al. |

It is certified that error appears in the above-identified patent and that said Letters Patent is hereby corrected as shown below:

Title Pg, please insert Item -- (60), Related U.S. Application Data
Provisional Application No. 60/346,288, filed on January 9, 2002. --

Signed and Sealed this

Twelfth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,354,577 B2
APPLICATION NO. : 10/497991
DATED : April 8, 2008
INVENTOR(S) : Jalkanen et al.

Page 1 of 1

It is certified that error appears in the above-identified patent and that said Letters Patent is hereby corrected as shown below:

<u>Column 6</u>
Line 51, please replace "3-372 (DSM ACC2590)" with --3-372 (DSM ACC2520)--.

<u>Column 17</u>
Line 59, please replace "3-372 (DSM ACC2590)" with --3-372 (DSM ACC2520)--.

<u>Column 41</u>
Line 42, please replace "the hybridoma DSM ACC2590" with --the hybridoma DSM ACC2520--.

<u>Column 42</u>
Line 37, please replace " the hybridoma DSM ACC2590" with --the hybridoma DSM ACC2520--.

<u>Column 42</u>
Lines 42-43, please replace "Antibody is said chimeric, humanized or primatized antibody" with
--The method of claim 1, wherein said antibody is said chimeric, humanized or primatized antibody--.

Signed and Sealed this

Sixth Day of July, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 7879
<212> TYPE: DNA
<213> ORGANISM: Homo sapiens
<220> FEATURE:
<221> NAME/KEY: exon
<222> LOCATION: (31)..(7740)

<400> SEQUENCE: 1

```
actctgtcct ggacagcgtg cccaccagcc atg gcg ggg ccc cgg ggc ctc ctc      54
                                Met Ala Gly Pro Arg Gly Leu Leu
                                 1               5 cca ctc tgc ctc ctg gcc ttc tgc ctg gca ggc ttc agc ttc gtc agg     102
Pro Leu Cys Leu Leu Ala Phe Cys Leu Ala Gly Phe Ser Phe Val Arg
    10                  15                  20 ggg cag gtg ctg ttc aaa ggc tgt gat gtg aaa acc acg ttt gtc act     150
```

-continued

| | | | | | | | | | | | | | | |
|---|---|---|---|---|---|---|---|---|---|---|---|---|---|---|
| Gly | Gln | Val | Leu | Phe | Lys | Gly | Cys | Asp | Val | Lys | Thr | Thr | Phe | Val | Thr |
| 25 | | | | | 30 | | | | | 35 | | | | | 40 |

| cat | gta | ccc | tgc | acc | tcg | tgc | gcg | gcc | atc | aag | aag | cag | acg | tgt | ccc | 198 |
|---|---|---|---|---|---|---|---|---|---|---|---|---|---|---|---|---|
| His | Val | Pro | Cys | Thr | Ser | Cys | Ala | Ala | Ile | Lys | Lys | Gln | Thr | Cys | Pro | |
| | | | | 45 | | | | | 50 | | | | | 55 | | |

| tca | ggc | tgg | ctg | cgg | gag | ctc | ccg | gat | cag | ata | acc | cag | gac | tgc | cgc | 246 |
|---|---|---|---|---|---|---|---|---|---|---|---|---|---|---|---|---|
| Ser | Gly | Trp | Leu | Arg | Glu | Leu | Pro | Asp | Gln | Ile | Thr | Gln | Asp | Cys | Arg | |
| | | | 60 | | | | | 65 | | | | | 70 | | | |

| tac | gaa | gta | cag | ctg | ggg | ggc | tct | atg | gtg | tcc | atg | agc | ggc | tgc | aga | 294 |
|---|---|---|---|---|---|---|---|---|---|---|---|---|---|---|---|---|
| Tyr | Glu | Val | Gln | Leu | Gly | Gly | Ser | Met | Val | Ser | Met | Ser | Gly | Cys | Arg | |
| | | 75 | | | | | 80 | | | | | 85 | | | | |

| cgg | aag | tgc | cgg | aag | caa | gtg | gtg | cag | aag | gcc | tgc | tgc | cct | ggc | tac | 342 |
|---|---|---|---|---|---|---|---|---|---|---|---|---|---|---|---|---|
| Arg | Lys | Cys | Arg | Lys | Gln | Val | Val | Gln | Lys | Ala | Cys | Cys | Pro | Gly | Tyr | |
| | 90 | | | | | 95 | | | | | 100 | | | | | |

| tgg | ggt | tcc | cgg | tgc | cat | gaa | tgc | cct | ggg | ggc | gct | gag | acc | cca | tgc | 390 |
|---|---|---|---|---|---|---|---|---|---|---|---|---|---|---|---|---|
| Trp | Gly | Ser | Arg | Cys | His | Glu | Cys | Pro | Gly | Gly | Ala | Glu | Thr | Pro | Cys | |
| 105 | | | | | 110 | | | | | 115 | | | | | 120 | |

| aat | ggc | cac | ggg | acc | tgc | ttg | gat | ggc | atg | gac | agg | aat | ggg | acc | tgt | 438 |
|---|---|---|---|---|---|---|---|---|---|---|---|---|---|---|---|---|
| Asn | Gly | His | Gly | Thr | Cys | Leu | Asp | Gly | Met | Asp | Arg | Asn | Gly | Thr | Cys | |
| | | | | 125 | | | | | 130 | | | | | 135 | | |

| gtg | tgc | cag | gaa | aac | ttc | cgc | ggc | tca | gcc | tgc | cag | gag | tgc | caa | gac | 486 |
|---|---|---|---|---|---|---|---|---|---|---|---|---|---|---|---|---|
| Val | Cys | Gln | Glu | Asn | Phe | Arg | Gly | Ser | Ala | Cys | Gln | Glu | Cys | Gln | Asp | |
| | | | 140 | | | | | 145 | | | | | 150 | | | |

| ccc | aac | cgg | ttc | ggg | cct | gac | tgc | caa | tcg | gtg | tgc | agc | tgt | gtg | cac | 534 |
|---|---|---|---|---|---|---|---|---|---|---|---|---|---|---|---|---|
| Pro | Asn | Arg | Phe | Gly | Pro | Asp | Cys | Gln | Ser | Val | Cys | Ser | Cys | Val | His | |
| | | 155 | | | | | 160 | | | | | 165 | | | | |

| gga | gtg | tgc | aac | cat | ggg | cca | cgt | ggg | gat | gga | agc | tgc | ctg | tgc | ttt | 582 |
|---|---|---|---|---|---|---|---|---|---|---|---|---|---|---|---|---|
| Gly | Val | Cys | Asn | His | Gly | Pro | Arg | Gly | Asp | Gly | Ser | Cys | Leu | Cys | Phe | |
| | 170 | | | | | 175 | | | | | 180 | | | | | |

| gct | gga | tac | act | ggc | ccc | cac | tgt | gat | caa | gag | ctg | ccc | gtc | tgc | cag | 630 |
|---|---|---|---|---|---|---|---|---|---|---|---|---|---|---|---|---|
| Ala | Gly | Tyr | Thr | Gly | Pro | His | Cys | Asp | Gln | Glu | Leu | Pro | Val | Cys | Gln | |
| 185 | | | | | 190 | | | | | 195 | | | | | 200 | |

| gag | ctg | cgc | tgt | ccc | cag | aac | acc | cag | tgc | tcc | gca | gag | gct | ccc | agc | 678 |
|---|---|---|---|---|---|---|---|---|---|---|---|---|---|---|---|---|
| Glu | Leu | Arg | Cys | Pro | Gln | Asn | Thr | Gln | Cys | Ser | Ala | Glu | Ala | Pro | Ser | |
| | | | | 205 | | | | | 210 | | | | | 215 | | |

| tgc | agg | tgc | ctg | ccc | ggc | tac | aca | cag | cag | ggc | agt | gaa | tgc | cga | gcc | 726 |
|---|---|---|---|---|---|---|---|---|---|---|---|---|---|---|---|---|
| Cys | Arg | Cys | Leu | Pro | Gly | Tyr | Thr | Gln | Gln | Gly | Ser | Glu | Cys | Arg | Ala | |
| | | | 220 | | | | | 225 | | | | | 230 | | | |

| ccc | aac | ccc | tgc | tgg | cca | tca | ccc | tgc | tca | ctg | ctg | gcc | cag | tgc | tcg | 774 |
|---|---|---|---|---|---|---|---|---|---|---|---|---|---|---|---|---|
| Pro | Asn | Pro | Cys | Trp | Pro | Ser | Pro | Cys | Ser | Leu | Leu | Ala | Gln | Cys | Ser | |
| | | 235 | | | | | 240 | | | | | 245 | | | | |

| gtg | agc | ccc | aag | ggg | cag | gct | cag | tgt | cac | tgc | cct | gag | aac | tac | cat | 822 |
|---|---|---|---|---|---|---|---|---|---|---|---|---|---|---|---|---|
| Val | Ser | Pro | Lys | Gly | Gln | Ala | Gln | Cys | His | Cys | Pro | Glu | Asn | Tyr | His | |
| | 250 | | | | | 255 | | | | | 260 | | | | | |

| ggc | gat | ggg | atg | gtg | tgt | ctg | ccc | aag | gac | cca | tgc | act | gac | aac | ctt | 870 |
|---|---|---|---|---|---|---|---|---|---|---|---|---|---|---|---|---|
| Gly | Asp | Gly | Met | Val | Cys | Leu | Pro | Lys | Asp | Pro | Cys | Thr | Asp | Asn | Leu | |
| 265 | | | | | 270 | | | | | 275 | | | | | 280 | |

| ggt | ggc | tgc | ccc | agc | aac | tct | act | ttg | tgt | gtg | tac | cag | aag | ccg | ggc | 918 |
|---|---|---|---|---|---|---|---|---|---|---|---|---|---|---|---|---|
| Gly | Gly | Cys | Pro | Ser | Asn | Ser | Thr | Leu | Cys | Val | Tyr | Gln | Lys | Pro | Gly | |
| | | | | 285 | | | | | 290 | | | | | 295 | | |

| cag | gcc | ttc | tgc | acc | tgc | cgg | cca | ggc | ctg | gtc | agc | atc | aac | agc | aac | 966 |
|---|---|---|---|---|---|---|---|---|---|---|---|---|---|---|---|---|
| Gln | Ala | Phe | Cys | Thr | Cys | Arg | Pro | Gly | Leu | Val | Ser | Ile | Asn | Ser | Asn | |
| | | | 300 | | | | | 305 | | | | | 310 | | | |

| gct | tct | gcg | ggc | tgc | ttc | gcc | ttc | tgc | tcc | ccc | ttc | tcc | tgc | gac | cgg | 1014 |
|---|---|---|---|---|---|---|---|---|---|---|---|---|---|---|---|---|
| Ala | Ser | Ala | Gly | Cys | Phe | Ala | Phe | Cys | Ser | Pro | Phe | Ser | Cys | Asp | Arg | |
| | | 315 | | | | | 320 | | | | | 325 | | | | |

| tct | gcc | act | tgc | cag | gtg | acc | gct | gat | ggg | aag | acc | agc | tgt | gtg | tgc | 1062 |
|---|---|---|---|---|---|---|---|---|---|---|---|---|---|---|---|---|
| Ser | Ala | Thr | Cys | Gln | Val | Thr | Ala | Asp | Gly | Lys | Thr | Ser | Cys | Val | Cys | |
| | 330 | | | | | 335 | | | | | 340 | | | | | |

-continued

| | | |
|---|---|---|
| agg gaa agc gag gtg ggg gat ggg cgt gcc tgc tac gga cac ctg ctc<br>Arg Glu Ser Glu Val Gly Asp Gly Arg Ala Cys Tyr Gly His Leu Leu<br>345                   350                     355                   360 | 1110 |
| cac gag gtg cag aag gcc acg cag aca ggc cgg gtg ttc ctg cag ctg<br>His Glu Val Gln Lys Ala Thr Gln Thr Gly Arg Val Phe Leu Gln Leu<br>                        365                     370                     375 | 1158 |
| agg gtc gcc gtg gcc atg atg gac cag ggc tgc cgg gaa atc ctt acc<br>Arg Val Ala Val Ala Met Met Asp Gln Gly Cys Arg Glu Ile Leu Thr<br>380                     385                     390 | 1206 |
| aca gcg ggc cct ttc acc gtg ctg gtg cca tcc gtc tcc tcc ttc tcc<br>Thr Ala Gly Pro Phe Thr Val Leu Val Pro Ser Val Ser Ser Phe Ser<br>                  395                    400                     405 | 1254 |
| tcc agg acc atg aat gca tcc ctt gcc cag cag ctc tgt aga cag cac<br>Ser Arg Thr Met Asn Ala Ser Leu Ala Gln Gln Leu Cys Arg Gln His<br>410                   415                     420 | 1302 |
| atc atc gca ggg cag cac atc ctg gag gac aca agg acc caa caa aca<br>Ile Ile Ala Gly Gln His Ile Leu Glu Asp Thr Arg Thr Gln Gln Thr<br>425                     430                     435                   440 | 1350 |
| cga agg tgg tgg acg ctg gcc ggg cag gag atc acc gtc acc ttt aac<br>Arg Arg Trp Trp Thr Leu Ala Gly Gln Glu Ile Thr Val Thr Phe Asn<br>                        445                     450                     455 | 1398 |
| caa ttc acg aaa tac tcc tac aag tac aaa gac cag ccc cag cag acg<br>Gln Phe Thr Lys Tyr Ser Tyr Lys Tyr Lys Asp Gln Pro Gln Gln Thr<br>                  460                     465                     470 | 1446 |
| ttc aac atc tac aag gcc aac aac ata gca gct aat ggc gtc ttc cac<br>Phe Asn Ile Tyr Lys Ala Asn Asn Ile Ala Ala Asn Gly Val Phe His<br>475                     480                     485 | 1494 |
| gtg gtc act ggc ctg cgg tgg cag gcc ccc tct ggg acc cct ggg gat<br>Val Val Thr Gly Leu Arg Trp Gln Ala Pro Ser Gly Thr Pro Gly Asp<br>490                   495                     500 | 1542 |
| ccc aag aga act atc gga cag atc ctc gcc tct acc gag gcc ttc agc<br>Pro Lys Arg Thr Ile Gly Gln Ile Leu Ala Ser Thr Glu Ala Phe Ser<br>505                     510                     515                   520 | 1590 |
| cgc ttt gaa acc atc ctg gag aac tgt ggg ctg ccc tcc atc ctg gac<br>Arg Phe Glu Thr Ile Leu Glu Asn Cys Gly Leu Pro Ser Ile Leu Asp<br>                        525                     530                   535 | 1638 |
| gga cct ggg ccc ttc aca gtc ttt gcc cca agc aat gag gct gtg gac<br>Gly Pro Gly Pro Phe Thr Val Phe Ala Pro Ser Asn Glu Ala Val Asp<br>                  540                     545                     550 | 1686 |
| agc ttg cgt gac ggc cgc ctg atc tac ctc ttc aca gcg ggt ctc tct<br>Ser Leu Arg Asp Gly Arg Leu Ile Tyr Leu Phe Thr Ala Gly Leu Ser<br>555                     560                     565 | 1734 |
| aaa ctg cag gag ttg gtg cgg tac cac atc tac aac cac ggc cag ctg<br>Lys Leu Gln Glu Leu Val Arg Tyr His Ile Tyr Asn His Gly Gln Leu<br>570                   575                     580 | 1782 |
| acc gtt gag aag ctc atc tcc aag ggt cgg atc ctc acc atg gcg aac<br>Thr Val Glu Lys Leu Ile Ser Lys Gly Arg Ile Leu Thr Met Ala Asn<br>585                     590                     595                   600 | 1830 |
| cag gtc ctg gct gtg aac att tct gag gag ggg cgc atc ctg ctg gga<br>Gln Val Leu Ala Val Asn Ile Ser Glu Glu Gly Arg Ile Leu Leu Gly<br>                        605                     610                     615 | 1878 |
| ccc gag ggg gtc ccg ctg cag agg gta gac gtg atg gcc gcc aat ggt<br>Pro Glu Gly Val Pro Leu Gln Arg Val Asp Val Met Ala Ala Asn Gly<br>                  620                     625                     630 | 1926 |
| gtg atc cac atg ctg gac ggc atc ctg ctg ccc ccg acc atc ctg ccc<br>Val Ile His Met Leu Asp Gly Ile Leu Leu Pro Pro Thr Ile Leu Pro<br>635                     640                     645 | 1974 |
| atc ctg ccc aag cac tgc agc gag gag cag cac aag att gtg gcg ggc<br>Ile Leu Pro Lys His Cys Ser Glu Glu Gln His Lys Ile Val Ala Gly<br>650                     655                     660 | 2022 |

```
                                                    -continued tcc tgt gtg gac tgc caa gcc ctg aac acc agc acg tgt ccc ccc aac    2070
Ser Cys Val Asp Cys Gln Ala Leu Asn Thr Ser Thr Cys Pro Pro Asn
665                 670                 675                 680 agt gtg aag ctg gac atc ttc ccc aag gag tgt gtc tac atc cat gac    2118
Ser Val Lys Leu Asp Ile Phe Pro Lys Glu Cys Val Tyr Ile His Asp
            685                 690                 695 cca acg ggg ctc aat gtg cta aag aag ggc tgt gcc agc tac tgc aac    2166
Pro Thr Gly Leu Asn Val Leu Lys Lys Gly Cys Ala Ser Tyr Cys Asn
        700                 705                 710 caa acc atc atg gaa caa ggc tgc tgc aaa ggt ttt ttc ggg cct gac    2214
Gln Thr Ile Met Glu Gln Gly Cys Cys Lys Gly Phe Phe Gly Pro Asp
    715                 720                 725 tgc acg cag tgt cct ggg ggc ttc tcc aac ccc tgc tat ggc aaa ggc    2262
Cys Thr Gln Cys Pro Gly Gly Phe Ser Asn Pro Cys Tyr Gly Lys Gly
730                 735                 740 aat tgc agt gat ggg atc cag ggc aat ggg gcc tgc ctc tgc ttc cca    2310
Asn Cys Ser Asp Gly Ile Gln Gly Asn Gly Ala Cys Leu Cys Phe Pro
745                 750                 755                 760 gac tac aag ggc atc gcc tgc cac atc tgc tcg aac cca aac aag cat    2358
Asp Tyr Lys Gly Ile Ala Cys His Ile Cys Ser Asn Pro Asn Lys His
            765                 770                 775 gga gag caa tgc cag gaa gac tgc ggc tgt gtc cat ggt ctc tgc gac    2406
Gly Glu Gln Cys Gln Glu Asp Cys Gly Cys Val His Gly Leu Cys Asp
        780                 785                 790 aac cgc cca ggc agt ggg ggg gtg tgc cag cag ggc acg tgt gcc cct    2454
Asn Arg Pro Gly Ser Gly Gly Val Cys Gln Gln Gly Thr Cys Ala Pro
    795                 800                 805 ggc ttc agt ggc cgg ttc tgc aac gag tcc atg ggg gac tgt ggg ccc    2502
Gly Phe Ser Gly Arg Phe Cys Asn Glu Ser Met Gly Asp Cys Gly Pro
810                 815                 820 aca ggg ctg gcc cag cac tgc cac ctg cat gcc cgc tgt gtt agc cag    2550
Thr Gly Leu Ala Gln His Cys His Leu His Ala Arg Cys Val Ser Gln
825                 830                 835                 840 gag ggt gtt gcc aga tgt cgc tgt ctt gat ggc ttt gag ggt gat ggc    2598
Glu Gly Val Ala Arg Cys Arg Cys Leu Asp Gly Phe Glu Gly Asp Gly
            845                 850                 855 ttc tcc tgc aca cct agc aac ccc tgc tcc cac ccg gac cgt gga ggc    2646
Phe Ser Cys Thr Pro Ser Asn Pro Cys Ser His Pro Asp Arg Gly Gly
        860                 865                 870 tgc tca gag aat gct gag tgt gtc cct ggg tcc ctg ggc acc cac cac    2694
Cys Ser Glu Asn Ala Glu Cys Val Pro Gly Ser Leu Gly Thr His His
    875                 880                 885 tgc aca tgc cac aaa ggc tgg agt ggg gat ggc cgc gtc tgt gtg gct    2742
Cys Thr Cys His Lys Gly Trp Ser Gly Asp Gly Arg Val Cys Val Ala
890                 895                 900 att gac gag tgt gag ctg gac gtg aga ggt ggc tgc cac acc gat gcc    2790
Ile Asp Glu Cys Glu Leu Asp Val Arg Gly Gly Cys His Thr Asp Ala
905                 910                 915                 920 ctc tgc agc tat gtg ggc ccc ggg cag agc cga tgc acc tgc aag ctg    2838
Leu Cys Ser Tyr Val Gly Pro Gly Gln Ser Arg Cys Thr Cys Lys Leu
            925                 930                 935 ggc ttt gcc ggg gat ggc tac cag tgc agc ccc atc gac ccc tgc cgg    2886
Gly Phe Ala Gly Asp Gly Tyr Gln Cys Ser Pro Ile Asp Pro Cys Arg
        940                 945                 950 gca ggc aat ggc ggc tgc cac ggc ctg gcc acc tgc cgg gca gtg ggg    2934
Ala Gly Asn Gly Gly Cys His Gly Leu Ala Thr Cys Arg Ala Val Gly
    955                 960                 965 gga ggt cag cgg gtc tgc acg tgc ccc cct ggc ttt ggg ggt gat ggc    2982
Gly Gly Gln Arg Val Cys Thr Cys Pro Pro Gly Phe Gly Gly Asp Gly
```

-continued

```
           970                 975                 980
ttc agc tgt tat gga gac atc ttc cgg gag ctg gag gca aat gcc cac       3030
Phe Ser Cys Tyr Gly Asp Ile Phe Arg Glu Leu Glu Ala Asn Ala His
985                 990                 995                 1000 ttc tcc atc ttc tac caa tgg ctt aag agt gcc ggc atc acg ctt           3075
Phe Ser Ile Phe Tyr Gln Trp Leu Lys Ser Ala Gly Ile Thr Leu
            1005                1010                1015 cct gcc gac cgc cga gtc aca gcc ctg gtg ccc tcc gag gct gca           3120
Pro Ala Asp Arg Arg Val Thr Ala Leu Val Pro Ser Glu Ala Ala
            1020                1025                1030 gtc cgt cag ctg agc ccc gag gac cga gct ttc tgg ctg cag cca           3165
Val Arg Gln Leu Ser Pro Glu Asp Arg Ala Phe Trp Leu Gln Pro
            1035                1040                1045 agg acg ctg ccg aac ctg gtc agg gcc cat ttt ctc cag ggt gcc           3210
Arg Thr Leu Pro Asn Leu Val Arg Ala His Phe Leu Gln Gly Ala
            1050                1055                1060 ctc ttc gag gag gag ctg gcc cgg ctg ggt ggg cag gaa gtg gcc           3255
Leu Phe Glu Glu Glu Leu Ala Arg Leu Gly Gly Gln Glu Val Ala
            1065                1070                1075 acc ctg aac ccc acc aca cgc tgg gag att cgc aac att agt ggg           3300
Thr Leu Asn Pro Thr Thr Arg Trp Glu Ile Arg Asn Ile Ser Gly
            1080                1085                1090 agg gtc tgg gtg cag aat gcc agc gtg gat gtg gct gac ctc ctt           3345
Arg Val Trp Val Gln Asn Ala Ser Val Asp Val Ala Asp Leu Leu
            1095                1100                1105 gcc acc aac ggt gtc cta cac atc ctc agc cag gtc tta ctg ccc           3390
Ala Thr Asn Gly Val Leu His Ile Leu Ser Gln Val Leu Leu Pro
            1110                1115                1120 ccc cga ggg gat gtg ccc ggt ggg cag ggg ttg ctg cag cag ctg           3435
Pro Arg Gly Asp Val Pro Gly Gly Gln Gly Leu Leu Gln Gln Leu
            1125                1130                1135 gac ttg gtg cct gcc ttc agc ctc ttc cgg gaa ttg ctg cag cac           3480
Asp Leu Val Pro Ala Phe Ser Leu Phe Arg Glu Leu Leu Gln His
            1140                1145                1150 cat ggg ttg gtg ccc cag att gag gct gcc act gcc tac acc atc           3525
His Gly Leu Val Pro Gln Ile Glu Ala Ala Thr Ala Tyr Thr Ile
            1155                1160                1165 ttt gtg ccc acc aac cgc tcc ctg gag gcc cag ggc aac agc agt           3570
Phe Val Pro Thr Asn Arg Ser Leu Glu Ala Gln Gly Asn Ser Ser
            1170                1175                1180 cac ctg gac gca gac aca gtg cgg cac cat gtg gtc ctg ggg gag           3615
His Leu Asp Ala Asp Thr Val Arg His His Val Val Leu Gly Glu
            1185                1190                1195 gcc ctc tcc atg gaa acc ctg cgg aag ggt gga cac cgc aac tcc           3660
Ala Leu Ser Met Glu Thr Leu Arg Lys Gly Gly His Arg Asn Ser
            1200                1205                1210 ctc ctg ggc cct gcc cac tgg atc gtc ttc tac aac cac agt ggc           3705
Leu Leu Gly Pro Ala His Trp Ile Val Phe Tyr Asn His Ser Gly
            1215                1220                1225 cag cct gag gtg aac cat gtg cca ctg gaa ggc ccc atg ctg gag           3750
Gln Pro Glu Val Asn His Val Pro Leu Glu Gly Pro Met Leu Glu
            1230                1235                1240 gcc cct ggc cgc tcg ctg att ggt ctg tcg ggg gtc ctg acg gtg           3795
Ala Pro Gly Arg Ser Leu Ile Gly Leu Ser Gly Val Leu Thr Val
            1245                1250                1255 ggc tca agt cgc tgc ctg cat agc cac gct gag gcc ctg cgg gag           3840
Gly Ser Ser Arg Cys Leu His Ser His Ala Glu Ala Leu Arg Glu
            1260                1265                1270 aaa tgt gta aac tgc acc agg aga ttc cgc tgc act cag ggc ttc           3885
```

```
                      -continued

Lys Cys Val Asn Cys  Thr Arg Arg Phe Arg  Cys Thr Gln Gly Phe
         1275                 1280                 1285 cag ctg cag gac aca  ccc agg aag agc tgt  gtc tac cga tct ggc        3930
Gln Leu Gln Asp Thr  Pro Arg Lys Ser Cys  Val Tyr Arg Ser Gly
         1290                 1295                 1300 ttc tcc ttc tcc cgg  ggc tgc tct tac aca  tgt gcc aag aag atc        3975
Phe Ser Phe Ser Arg  Gly Cys Ser Tyr Thr  Cys Ala Lys Lys Ile
         1305                 1310                 1315 cag gtg ccg gac tgc  tgc cct ggt ttc ttt  ggc acg ctg tgt gag        4020
Gln Val Pro Asp Cys  Cys Pro Gly Phe Phe  Gly Thr Leu Cys Glu
         1320                 1325                 1330 cca tgc cca ggg ggt  cta ggg ggg gtg tgc  tca ggc cat ggg cag        4065
Pro Cys Pro Gly Gly  Leu Gly Gly Val Cys  Ser Gly His Gly Gln
         1335                 1340                 1345 tgc cag gac agg ttc  ctg ggc agc ggg gag  tgc cac tgc cac gag        4110
Cys Gln Asp Arg Phe  Leu Gly Ser Gly Glu  Cys His Cys His Glu
         1350                 1355                 1360 ggc ttc cat gga acg  gcc tgt gag gtg tgt  gag ctg ggc cgc tac        4155
Gly Phe His Gly Thr  Ala Cys Glu Val Cys  Glu Leu Gly Arg Tyr
         1365                 1370                 1375 ggg ccc aac tgc acc  gga gtg tgt gac tgt  gcc cat ggg ctg tgc        4200
Gly Pro Asn Cys Thr  Gly Val Cys Asp Cys  Ala His Gly Leu Cys
         1380                 1385                 1390 cag gag ggg ctg caa  ggg gac gga agc tgt  gtc tgt aac gtg ggc        4245
Gln Glu Gly Leu Gln  Gly Asp Gly Ser Cys  Val Cys Asn Val Gly
         1395                 1400                 1405 tgg cag ggc ctc cgc  tgt gac cag aaa atc  acc agc cct cag tgc        4290
Trp Gln Gly Leu Arg  Cys Asp Gln Lys Ile  Thr Ser Pro Gln Cys
         1410                 1415                 1420 cct agg aag tgc gac  ccc aat gcc aac tgc  gtg cag gac tcg gcc        4335
Pro Arg Lys Cys Asp  Pro Asn Ala Asn Cys  Val Gln Asp Ser Ala
         1425                 1430                 1435 gga gcc tcc acc tgc  gcc tgt gct gcg gga  tac tcc ggc aat ggc        4380
Gly Ala Ser Thr Cys  Ala Cys Ala Ala Gly  Tyr Ser Gly Asn Gly
         1440                 1445                 1450 atc ttc tgt tca gag  gtg gac ccc tgc gcc  cac ggc cat ggg ggc        4425
Ile Phe Cys Ser Glu  Val Asp Pro Cys Ala  His Gly His Gly Gly
         1455                 1460                 1465 tgc tcc cct cat gcc  aac tgt acc aag gtg  gca cct ggg cag cgg        4470
Cys Ser Pro His Ala  Asn Cys Thr Lys Val  Ala Pro Gly Gln Arg
         1470                 1475                 1480 aca tgc acc tgc cag  gat ggc tac atg ggc  gac ggg gag ctg tgc        4515
Thr Cys Thr Cys Gln  Asp Gly Tyr Met Gly  Asp Gly Glu Leu Cys
         1485                 1490                 1495 cag gaa att aac agc  tgt ctc atc cac cac  ggg ggc tgc cac att        4560
Gln Glu Ile Asn Ser  Cys Leu Ile His His  Gly Gly Cys His Ile
         1500                 1505                 1510 cac gcc gag tgc atc  ccc act ggc ccc cag  cag gtc tcc tgc agc        4605
His Ala Glu Cys Ile  Pro Thr Gly Pro Gln  Gln Val Ser Cys Ser
         1515                 1520                 1525 tgc cgt gag ggt tac  agc ggg gat ggc atc  cgg acc tgc gag ctc        4650
Cys Arg Glu Gly Tyr  Ser Gly Asp Gly Ile  Arg Thr Cys Glu Leu
         1530                 1535                 1540 ctg gac ccc tgc tct  aag aac aat gga gga  tgc agc cca tat gcc        4695
Leu Asp Pro Cys Ser  Lys Asn Asn Gly Gly  Cys Ser Pro Tyr Ala
         1545                 1550                 1555 acc tgc aaa agc aca  ggg gat ggc cag agg  aca tgt acc tgc gac        4740
Thr Cys Lys Ser Thr  Gly Asp Gly Gln Arg  Thr Cys Thr Cys Asp
         1560                 1565                 1570
```

```
aca gcc cac acc gtg ggg gac ggc ctc acc tgc gtg gcc cga gtc         4785
Thr Ala His Thr Val Gly Asp Gly Leu Thr Cys Arg Ala Arg Val
              1575                1580                1585 ggc ctg gag ctc ctg agg gat aag cat gcc tca ttc ttc agc ctc         4830
Gly Leu Glu Leu Leu Arg Asp Lys His Ala Ser Phe Phe Ser Leu
              1590                1595                1600 cgc ctc ctg gaa tat aag gag ctc aag ggc gat ggg cct ttc acc         4875
Arg Leu Leu Glu Tyr Lys Glu Leu Lys Gly Asp Gly Pro Phe Thr
              1605                1610                1615 atc ttc gtg ccg cac gca gat cta atg agc aac ctg tcg cag gat         4920
Ile Phe Val Pro His Ala Asp Leu Met Ser Asn Leu Ser Gln Asp
              1620                1625                1630 gag ctg gcc cgg att cgt gcg cat cgc cag ctg gtg ttt cgc tac         4965
Glu Leu Ala Arg Ile Arg Ala His Arg Gln Leu Val Phe Arg Tyr
              1635                1640                1645 cac gtg gtt ggc tgt cgg cgg ctg cgg agc gag gac ctg ctg gag         5010
His Val Val Gly Cys Arg Arg Leu Arg Ser Glu Asp Leu Leu Glu
              1650                1655                1660 cag ggg tac gcc acg gcc ctc tca ggg cac cca ctg cgc ttc agc         5055
Gln Gly Tyr Ala Thr Ala Leu Ser Gly His Pro Leu Arg Phe Ser
              1665                1670                1675 gag agg gag ggc agc ata tac ctc aat gac ttc gcg cgc gtg gtg         5100
Glu Arg Glu Gly Ser Ile Tyr Leu Asn Asp Phe Ala Arg Val Val
              1680                1685                1690 agc agc gac cat gag gcc gtg aac ggc atc ctg cac ttc att gac         5145
Ser Ser Asp His Glu Ala Val Asn Gly Ile Leu His Phe Ile Asp
              1695                1700                1705 cgt gtc ctg ctg ccc ccc gag gcg ctg cac tgg gag cct gat gat         5190
Arg Val Leu Leu Pro Pro Glu Ala Leu His Trp Glu Pro Asp Asp
              1710                1715                1720 gct ccc atc ccg agg aga aat gtc acc gcc gcc gcc cag ggc ttc         5235
Ala Pro Ile Pro Arg Arg Asn Val Thr Ala Ala Ala Gln Gly Phe
              1725                1730                1735 ggt tac aag atc ttc agc ggc ctc ctg aag gtg gcc ggc ctc ctg         5280
Gly Tyr Lys Ile Phe Ser Gly Leu Leu Lys Val Ala Gly Leu Leu
              1740                1745                1750 ccc ctg ctt cga gag gca tcc cat agg ccc ttc aca atg ctg tgg         5325
Pro Leu Leu Arg Glu Ala Ser His Arg Pro Phe Thr Met Leu Trp
              1755                1760                1765 ccc aca gac gcc gcc ttt cga gct ctg cct ccg gat cgc cag gcc         5370
Pro Thr Asp Ala Ala Phe Arg Ala Leu Pro Pro Asp Arg Gln Ala
              1770                1775                1780 tgg ctg tac cat gag gac cac cgt gac aag cta gca gcc att ctg         5415
Trp Leu Tyr His Glu Asp His Arg Asp Lys Leu Ala Ala Ile Leu
              1785                1790                1795 cgg ggc cac atg att cgc aat gtc gag gcc ttg gca tct gac ctg         5460
Arg Gly His Met Ile Arg Asn Val Glu Ala Leu Ala Ser Asp Leu
              1800                1805                1810 ccc aac ctg ggc cca ctt cga acc atg cat ggg acc ccc atc tct         5505
Pro Asn Leu Gly Pro Leu Arg Thr Met His Gly Thr Pro Ile Ser
              1815                1820                1825 ttc tcc tgc agc cga acg cgg ccc ggt gag ctc atg gtg ggt gag         5550
Phe Ser Cys Ser Arg Thr Arg Pro Gly Glu Leu Met Val Gly Glu
              1830                1835                1840 gat gat gct cgc att gtg cag cgg cac ttg ccc ttt gag ggt ggc         5595
Asp Asp Ala Arg Ile Val Gln Arg His Leu Pro Phe Glu Gly Gly
              1845                1850                1855 ctg gcc tat ggc atc gac cag ctg ctg gag cca cct ggc ctt ggt         5640
Leu Ala Tyr Gly Ile Asp Gln Leu Leu Glu Pro Pro Gly Leu Gly
              1860                1865                1870
```

```
                                   -continued gct cgc tgt gac cac ttt gag acc cgg ccc ctg cga ctg aac acc      5685
Ala Arg Cys Asp His Phe Glu Thr Arg Pro Leu Arg Leu Asn Thr
            1875                1880                1885 tgc agc atc tgt ggg ctg gag cca ccc tgt cct gag ggg tca cag      5730
Cys Ser Ile Cys Gly Leu Glu Pro Pro Cys Pro Glu Gly Ser Gln
            1890                1895                1900 gag cag ggc agc cct gag gcc tgc tgg cgc ttc tac ccg aag ttc      5775
Glu Gln Gly Ser Pro Glu Ala Cys Trp Arg Phe Tyr Pro Lys Phe
            1905                1910                1915 tgg acg tcc cct ccg ctg cac tct ttg gga tta cgc agc gtc tgg      5820
Trp Thr Ser Pro Pro Leu His Ser Leu Gly Leu Arg Ser Val Trp
            1920                1925                1930 gtc cac ccc agc ctt tgg ggt agg ccc caa ggc ctg ggc agg ggc      5865
Val His Pro Ser Leu Trp Gly Arg Pro Gln Gly Leu Gly Arg Gly
            1935                1940                1945 tgc cac cgc aat tgt gtc acc acc acc tgg aag ccc agc tgc tgc      5910
Cys His Arg Asn Cys Val Thr Thr Thr Trp Lys Pro Ser Cys Cys
            1950                1955                1960 cct ggt cac tat ggc agt gag tgc caa gct tgc cct ggc ggc ccc      5955
Pro Gly His Tyr Gly Ser Glu Cys Gln Ala Cys Pro Gly Gly Pro
            1965                1970                1975 agc agc cct tgt agt gac cgt ggc gtg tgc atg gac ggc atg agt      6000
Ser Ser Pro Cys Ser Asp Arg Gly Val Cys Met Asp Gly Met Ser
            1980                1985                1990 ggc agt ggg cag tgt ctg tgc cgt tca ggt ttt gct ggg aca gcc      6045
Gly Ser Gly Gln Cys Leu Cys Arg Ser Gly Phe Ala Gly Thr Ala
            1995                2000                2005 tgt gaa ctc tgt gct cct ggt gcc ttt ggg ccc cat tgt caa gcc      6090
Cys Glu Leu Cys Ala Pro Gly Ala Phe Gly Pro His Cys Gln Ala
            2010                2015                2020 tgc cgc tgc act gtg cat ggc cgc tgt gat gag ggc ctt ggg ggc      6135
Cys Arg Cys Thr Val His Gly Arg Cys Asp Glu Gly Leu Gly Gly
            2025                2030                2035 tct ggc tcc tgc ttc tgt gat gaa ggc tgg act ggg cca cgc tgt      6180
Ser Gly Ser Cys Phe Cys Asp Glu Gly Trp Thr Gly Pro Arg Cys
            2040                2045                2050 gag gtg caa ctg gag ctg cag cct gtg tgt acc cca ccc tgt gca      6225
Glu Val Gln Leu Glu Leu Gln Pro Val Cys Thr Pro Pro Cys Ala
            2055                2060                2065 ccc gag gct gtg tgc cgt gca ggc aac agc tgt gag tgc agc ctg      6270
Pro Glu Ala Val Cys Arg Ala Gly Asn Ser Cys Glu Cys Ser Leu
            2070                2075                2080 ggc tat gaa ggg gat ggc cgc gtg tgt aca gtg gca gac ctg tgc      6315
Gly Tyr Glu Gly Asp Gly Arg Val Cys Thr Val Ala Asp Leu Cys
            2085                2090                2095 cag gac ggg cat ggt ggc tgc agt gag cac gcc aac tgt agc cag      6360
Gln Asp Gly His Gly Gly Cys Ser Glu His Ala Asn Cys Ser Gln
            2100                2105                2110 gta gga aca atg gtc act tgt acc tgc ctg ccc gac tac gag ggt      6405
Val Gly Thr Met Val Thr Cys Thr Cys Leu Pro Asp Tyr Glu Gly
            2115                2120                2125 gat ggc tgg agc tgc cgg gcc cgc aac ccc tgc aca gat ggc cac      6450
Asp Gly Trp Ser Cys Arg Ala Arg Asn Pro Cys Thr Asp Gly His
            2130                2135                2140 cgc ggg ggc tgc agc gag cac gcc aac tgc ttg agc acc ggc ctg      6495
Arg Gly Gly Cys Ser Glu His Ala Asn Cys Leu Ser Thr Gly Leu
            2145                2150                2155 aac aca cgg cgc tgt gag tgc cac gca ggc tac gta ggc gat gga      6540
Asn Thr Arg Arg Cys Glu Cys His Ala Gly Tyr Val Gly Asp Gly
```

-continued

```
                  2160              2165              2170
ctg cag tgt ctg gag  gag tcg gaa cca cct  gtg gac cgc tgc ttg              6585
Leu Gln Cys Leu Glu  Glu Ser Glu Pro Pro  Val Asp Arg Cys Leu
            2175              2180              2185 ggc cag cca ccg ccc  tgc cac tca gat gcc  atg tgc act gac ctg              6630
Gly Gln Pro Pro Pro  Cys His Ser Asp Ala  Met Cys Thr Asp Leu
            2190              2195              2200 cac ttc cag gag aaa  cgg gct ggc gtt ttc  cac ctc cag gcc acc              6675
His Phe Gln Glu Lys  Arg Ala Gly Val Phe  His Leu Gln Ala Thr
            2205              2210              2215 agc ggc cct tat ggt  ctg aac ttt tcg gag  gct gag gcg gca tgc              6720
Ser Gly Pro Tyr Gly  Leu Asn Phe Ser Glu  Ala Glu Ala Ala Cys
            2220              2225              2230 gaa gca cag gga gcc  gtc ctt gct tca ttc  cct cag ctc tct gct              6765
Glu Ala Gln Gly Ala  Val Leu Ala Ser Phe  Pro Gln Leu Ser Ala
            2235              2240              2245 gcc cag cag ctg ggc  ttc cac ctg tgc ctc  atg ggc tgg ctg gcc              6810
Ala Gln Gln Leu Gly  Phe His Leu Cys Leu  Met Gly Trp Leu Ala
            2250              2255              2260 aat ggc tcc act gcc  cac cct gtg gtt ttc  cct gtg gcg gac tgt              6855
Asn Gly Ser Thr Ala  His Pro Val Val Phe  Pro Val Ala Asp Cys
            2265              2270              2275 ggc aat ggt cgg gtg  ggc gta gtc agc ctg  ggt gcc cgc aag aac              6900
Gly Asn Gly Arg Val  Gly Val Val Ser Leu  Gly Ala Arg Lys Asn
            2280              2285              2290 ctc tca gaa cgc tgg  gat gcc tac tgc ttc  cgt gtg caa gat gtg              6945
Leu Ser Glu Arg Trp  Asp Ala Tyr Cys Phe  Arg Val Gln Asp Val
            2295              2300              2305 gcc tgc cga tgc cga  aat ggc ttc gtg ggt  gac ggg atc agc acg              6990
Ala Cys Arg Cys Arg  Asn Gly Phe Val Gly  Asp Gly Ile Ser Thr
            2310              2315              2320 tgc aat ggg aag ctg  ctg gat gtg ctg gct  gcc act gcc aac ttc              7035
Cys Asn Gly Lys Leu  Leu Asp Val Leu Ala  Ala Thr Ala Asn Phe
            2325              2330              2335 tcc acc ttc tat ggg  atg cta ttg ggc tat  gcc aat gcc acc cag              7080
Ser Thr Phe Tyr Gly  Met Leu Leu Gly Tyr  Ala Asn Ala Thr Gln
            2340              2345              2350 cgg ggt ctc gac ttc  ctg gac ttc ctg gat  gat gag ctc acg tat              7125
Arg Gly Leu Asp Phe  Leu Asp Phe Leu Asp  Asp Glu Leu Thr Tyr
            2355              2360              2365 aag aca ctc ttc gtc  cct gtc aat gaa ggc  ttt gtg gac aac atg              7170
Lys Thr Leu Phe Val  Pro Val Asn Glu Gly  Phe Val Asp Asn Met
            2370              2375              2380 acg ctg agt ggc cca  gac ttg gag ctg cat  gcc tcc aac gcc acc              7215
Thr Leu Ser Gly Pro  Asp Leu Glu Leu His  Ala Ser Asn Ala Thr
            2385              2390              2395 ctc cta agt gcc aac  gcc agc cag ggg aag  ttg ctt ccg gcc cac              7260
Leu Leu Ser Ala Asn  Ala Ser Gln Gly Lys  Leu Leu Pro Ala His
            2400              2405              2410 tca ggc ctc agc ctc  atc atc agt gac gca  ggc cct gac aac agt              7305
Ser Gly Leu Ser Leu  Ile Ile Ser Asp Ala  Gly Pro Asp Asn Ser
            2415              2420              2425 tcc tgg gcc cct gtg  gcc cca ggg aca gtt  gtg gtt agc cgt atc              7350
Ser Trp Ala Pro Val  Ala Pro Gly Thr Val  Val Val Ser Arg Ile
            2430              2435              2440 att gtg tgg gac atc  atg gcc ttc aat ggc  atc atc cat gct ctg              7395
Ile Val Trp Asp Ile  Met Ala Phe Asn Gly  Ile Ile His Ala Leu
            2445              2450              2455 gcc agc ccc ctc ctg  gca ccc cca cag ccc  cag gca gtg ctg gcg              7440
```

-continued

```
Ala Ser Pro Leu Leu Ala Pro Pro Gln Pro Gln Ala Val Leu Ala
            2460            2465            2470 cct gaa gcc cca cct gtg gcg gca ggc gtg ggg gct gtg ctt gcc      7485
Pro Glu Ala Pro Pro Val Ala Ala Gly Val Gly Ala Val Leu Ala
            2475            2480            2485 gct gga gca ctg ctt ggc ttg gtg gcc gga gct ctc tac ctc cgt      7530
Ala Gly Ala Leu Leu Gly Leu Val Ala Gly Ala Leu Tyr Leu Arg
            2490            2495            2500 gcc cga ggc aag ccc acg ggc ttt ggc ttc tct gcc ttc cag gcg      7575
Ala Arg Gly Lys Pro Thr Gly Phe Gly Phe Ser Ala Phe Gln Ala
            2505            2510            2515 gaa gat gat gct gac gac gac ttc tca ccg tgg caa gaa ggg acc      7620
Glu Asp Asp Ala Asp Asp Asp Phe Ser Pro Trp Gln Glu Gly Thr
            2520            2525            2530 aac ccc acc ctg gtc tct gtc ccc aac cct gtc ttt ggc agc gac      7665
Asn Pro Thr Leu Val Ser Val Pro Asn Pro Val Phe Gly Ser Asp
            2535            2540            2545 acc ttt tgt gaa ccc ttc gat gac tca ctg ctg gag gag gac ttc      7710
Thr Phe Cys Glu Pro Phe Asp Asp Ser Leu Leu Glu Glu Asp Phe
            2550            2555            2560 cct gac acc cag agg atc ctc aca gtc aag tgacgaggct ggggctgaaa   7760
Pro Asp Thr Gln Arg Ile Leu Thr Val Lys
            2565            2570 gcagaagcat gcacagggag gagaccactt ttattgcttg tctgggtgga tgggcagga  7820 ggggctgagg gcctgtccca gacaataaag tgccctcagc ggatgtgggc catgtcacc  7879
```